(12) United States Patent
Pfefferle et al.

(10) Patent No.: US 9,155,577 B2
(45) Date of Patent: Oct. 13, 2015

(54) HOUSING FOR A LOCKING ELEMENT AND LOCKING ELEMENT

(75) Inventors: Joachim Pfefferle, Munstertal (DE); Hermann Zeuner, Freiburg (DE); Peter Scheuble, Schliengen (DE); Matthias Walter, Emmendingen (DE); Dirk Thiel, Staufen (DE)

(73) Assignee: Medartis AG, Basel (CH)

(*) Notice: Subject to any disclaimer, the term of this patent is extended or adjusted under 35 U.S.C. 154(b) by 2553 days.

(21) Appl. No.: 10/550,383

(22) PCT Filed: Mar. 26, 2004

(86) PCT No.: PCT/CH2004/000188
§ 371 (c)(1),
(2), (4) Date: Jun. 13, 2006

(87) PCT Pub. No.: WO2004/086990
PCT Pub. Date: Oct. 14, 2004

(65) Prior Publication Data
US 2007/0043366 A1 Feb. 22, 2007

(30) Foreign Application Priority Data

Apr. 3, 2003 (CH) .......................................... 592/03
Sep. 23, 2003 (CH) ....................................... 1621/03

(51) Int. Cl.
*A61B 17/84* (2006.01)
*A61B 17/80* (2006.01)
(Continued)

(52) U.S. Cl.
CPC ......... *A61B 17/8061* (2013.01); *A61B 17/8052* (2013.01); *A61B 17/8004* (2013.01); *A61B 17/8085* (2013.01); *A61B 2017/8655* (2013.01); *F16B 5/0216* (2013.01); *F16B 35/06* (2013.01)

(58) Field of Classification Search
USPC ........ 606/280–33, 70, 71; 411/417, 418, 311, 411/437, 166, 354
See application file for complete search history.

(56) References Cited

U.S. PATENT DOCUMENTS 388,000 A * 8/1888 Rider ............................ 411/399
1,151,861 A * 8/1915 Brumback .................... 411/399
(Continued)

FOREIGN PATENT DOCUMENTS

EP 0 146 872 A2 7/1985
EP 0 517 939 A1 12/1992
(Continued)

OTHER PUBLICATIONS http://en.wikipedia.org/wiki/Fermat's_spiral, Fermat Spiral, accessed Jan. 13, 2014.*
(Continued)

*Primary Examiner* — Jan Christopher Merene
(74) *Attorney, Agent, or Firm* — Hahn Loeser & Parks LLP

(57) ABSTRACT

A locking element and a corresponding housing are disclosed, for the locking of the locking element in housing. The locking element includes a locking piece, for example a head, with a peripheral outer surface, running essentially in the direction of a longitudinal axis with at least one clamping surface extending outwards from the longitudinal axis in the form of a wedge, in order to lock the locking piece on the locking element with a corresponding inner contour of the housing. The peripheral outer surface is at least approximately spherical, parabolic, elliptical or hyperbolic in embodiment, viewed in the direction of the longitudinal axis in the region of the clamping surface, which is also true for the inner contour of the housing in the region of the recess, whereby the recess cooperating with the clamping surface can also be cylindrical.

21 Claims, 26 Drawing Sheets

(51) Int. Cl.
   *A61B 17/86* (2006.01)
   *F16B 5/02* (2006.01)
   *F16B 35/06* (2006.01)

(56) References Cited

U.S. PATENT DOCUMENTS

| | | | | |
|---|---|---|---|---|
| 2,135,637 | A | * | 11/1938 | Gade .............. 411/311 |
| 2,136,524 | A | * | 11/1938 | Rosenberg .............. 470/11 |
| 2,284,847 | A | * | 6/1942 | Raymond .............. 403/350 |
| 2,346,346 | A | | 4/1944 | Anderson |
| 2,479,698 | A | * | 8/1949 | Paquin .............. 173/133 |
| 4,095,914 | A | | 6/1978 | Thomsen |
| 4,127,119 | A | | 11/1978 | Kronner |
| 4,135,505 | A | | 1/1979 | Day |
| 4,347,636 | A | * | 9/1982 | Capuano .............. 470/25 |
| 4,620,533 | A | | 11/1986 | Mears |
| 4,621,627 | A | | 11/1986 | DeBastiani et al. |
| 4,858,601 | A | * | 8/1989 | Glisson .............. 606/916 |
| 4,890,631 | A | | 1/1990 | Hardy |
| 4,941,481 | A | | 7/1990 | Wagenknecht |
| 5,275,601 | A | * | 1/1994 | Gogolewski et al. ......... 606/291 |
| 5,290,288 | A | | 3/1994 | Vignaud et al. |
| 5,393,161 | A | | 2/1995 | Mata et al. |
| 5,407,295 | A | | 4/1995 | Kuhl |
| 5,456,719 | A | * | 10/1995 | Keller .............. 623/11.11 |
| 5,674,036 | A | | 10/1997 | Hsieh |
| 5,702,394 | A | | 12/1997 | Henry et al. |
| 5,709,686 | A | | 1/1998 | Talos et al. |
| 5,807,396 | A | | 9/1998 | Raveh |
| 5,993,450 | A | | 11/1999 | Worcel |
| 6,206,881 | B1 | * | 3/2001 | Frigg et al. .............. 606/291 |
| 6,322,562 | B1 | | 11/2001 | Wolter |
| 6,343,531 | B2 | * | 2/2002 | Amis .............. 81/121.1 |
| 6,572,622 | B1 | | 6/2003 | Schafer et al. .............. 606/272 |
| 6,730,091 | B1 | * | 5/2004 | Pfefferle et al. .............. 606/70 |
| 7,077,844 | B2 | * | 7/2006 | Michelson .............. 606/71 |
| 7,229,442 | B2 | * | 6/2007 | Schafer .............. 606/272 |
| 7,513,913 | B2 | * | 4/2009 | Hoermansdoerfer ...... 623/22.31 |
| 7,527,639 | B2 | * | 5/2009 | Orbay et al. .............. 606/287 |
| 8,753,379 | B1 | | 6/2014 | Frei et al. |
| 2001/0021851 | A1 | * | 9/2001 | Eberlein et al. .............. 606/69 |
| 2002/0026190 | A1 | | 2/2002 | Walulik et al. |
| 2002/0045901 | A1 | | 4/2002 | Wagner et al. |
| 2002/0128655 | A1 | * | 9/2002 | Michelson .............. 606/70 |
| 2003/0078583 | A1 | | 4/2003 | Biedermann et al. |
| 2003/0149429 | A1 | | 8/2003 | Ferrante et al. |
| 2003/0171754 | A1 | | 9/2003 | Del Medico |
| 2003/0187439 | A1 | | 10/2003 | Biedermann et al. |
| 2004/0059330 | A1 | | 3/2004 | Biedermann et al. |
| 2004/0073218 | A1 | * | 4/2004 | Dahners .............. 606/69 |
| 2004/0127899 | A1 | | 7/2004 | Konieczynski et al. |
| 2005/0038521 | A1 | * | 2/2005 | Hoermansdoerfer ...... 623/22.31 |
| 2005/0043736 | A1 | * | 2/2005 | Mathieu et al. .............. 606/73 |
| 2005/0143742 | A1 | | 6/2005 | Porcher |
| 2005/0165400 | A1 | * | 7/2005 | Fernandez .............. 606/69 |
| 2005/0216003 | A1 | | 9/2005 | Biedermann et al. |
| 2005/0222570 | A1 | | 10/2005 | Jackson |
| 2006/0058797 | A1 | * | 3/2006 | Mathieu et al. .............. 606/69 |
| 2006/0195104 | A1 | | 8/2006 | Schlafli et al. |
| 2007/0083207 | A1 | * | 4/2007 | Ziolo et al. .............. 606/73 |

FOREIGN PATENT DOCUMENTS

| | | |
|---|---|---|
| GB | 2 031 731 A | 4/1980 |
| JP | 63 158 308 A2 | 7/1988 |
| WO | WO 94/07040 | 3/1994 |
| WO | WO 0075737 A1 * 12/2000 | ............ G05B 19/18 |

OTHER PUBLICATIONS

"Paraboloid" (Wikipedia Oct. 10, 2013).

* cited by examiner

HOUSING FOR A LOCKING ELEMENT AND LOCKING ELEMENT

FIELD OF THE INVENTION

The invention relates to a housing for a locking element.

RELATED APPLICATIONS

This application is a 35 USC Section 371 application of PCT/CH04/00188 filed Mar. 26, 2004, which claims Foreign Priority to CH 592/03 filed Apr. 4, 2003 and CH 1621/03 filed Sep. 23, 2003.

BACKGROUND

Depending on their type, such housings and locking elements are used for the connection of various elements in cases where such elements are to be connected fixedly to one another, for example in general mechanical engineering (e.g. in shaft-hub connections, as are known from DE-A-42 09 153, or in other connections, e.g. in screw connections where two structural parts are to be locked fixedly to one another).

A specific field of application of such connections is the field of medical engineering, for example the field of traumatology, where it is not uncommon to perform fixation of bone segments, for example in fractures. For optimal treatment of the fractures, the individual bone segments have to be repositioned as exactly as possible and have to be fixed in the desired position with the aid of a bone plate and bone screws, to ensure that treatment is as successful as possible.

For successful treatment, it is important, after they have been fixed, that the bone segments remain stable with the aid of the bone plate; for example, a bone screw must not come loose from the bone plate, as can happen, for example, in rare cases of undesired loading of a treated fracture. In such cases, the bone segments may then assume a position different than the desired position, which may reduce the degree of success of the treatment.

WO-A-00/66012 has already proposed a bone plate in which an engagement contour made in the plate aperture has a plurality of horizontally and radially extending contour valleys and, adjacent to these, contour peaks. However, the engagement contour does not extend completely round the plate aperture, and instead runs out at two horizontally opposite ends. There, uncontoured wall areas remain in the plate aperture, as a result of which the plate aperture has an oblong hole shape. The associated bone screw has a bone thread on its shank, and above the bone thread, but below the screw head, there is an additional locking thread. While the bone thread is screwed in the usual manner into the bone segment, the locking thread engages in the engagement contour of the plate aperture in the final phase of screwing-in of the bone screw. Since the locking thread with its helical course and its pitch does not complement the engagement contour in the plate aperture, this causes deformation of both parts and, therefore, a strong connection of bone plate and bone screw and, although this connection can in principle be released again, automatic loosening of the screw is reliably avoided.

For example, when two bone segments, namely a first bone segment on one side of a fracture and a second bone segment on the other side of the fracture, are brought into a desired position relative to one another, a bone screw is screwed into each of the two bone segments via the plate aperture of the bone plate, and the bone screws are locked in the plate aperture of the bone plate, so that the bone segments remain in the desired position after locking. The stable locking in the plate aperture also ensures, inter alia, that the bone plate does not have to lie on the bone, and instead, for example, can also be arranged in a stable manner at a short distance from the bone. This may be of advantage, because the periosteum ensures better blood circulation and nutrition of the bone, and an intact periosteum thus promotes the healing process. This very functionally reliable bone plate described in WO-A-00/66012 allows the screw to be introduced with a slight deviation from the perpendicular axis of screwing; the perpendicular axis of the plate aperture and the actual direction of screwing can therefore enclose a small angle between each other. However, such a deviation of the actual axis of screwing from the perpendicular axis of the plate aperture (tilting of the actual axis of screwing relative to the perpendicular axis of the plate aperture) can only be present in the direction of the longer axis of the oblong plate aperture (that is to say in the direction of the two ends of the plate aperture with the uncontoured wall areas), and it is possible only within a relatively small angle range.

In many cases, however, it would be advantageous for the operating surgeon to be able to fit a bone screw as freely as possible in respect of direction, for example if a fracture to be treated lies outside the access route, or if the amount of available bone substance is such that the screw would be best fitted in a specific direction. It should further be noted that, in many cases, subsequent repositioning of a bone segment may be desirable. Although this is possible in principle in the bone plate known from WO-A-00/66012, such repositioning is more difficult because of the deformation of locking thread and engagement contour. However, in complicated fractures in particular, with several bone segments, in some cases with small bone segments, for example in the region of the hand, it is often very important, for optimal positioning of the individual bone segments, that the locking can be released again without damaging the screw and/or the plate and that individual bone segments are able to a certain extent to be positioned differently.

SUMMARY

This is what the present invention is for, its general object being to provide a connection, that is to say both a housing and also a corresponding locking element, which connection is highly flexible and at the same time reliable. In particular, locking should be possible in different directions and at different angles (that is to say not just in one direction). In addition, it should also be possible, after initial locking, to easily release the locking and then perform renewed locking, without damaging the housing (e.g. the plate aperture of the bone plate) or the locking element (e.g. the screw). At the same time, a secure connection should be produced which does not permit automatic loosening of the locking element (e.g. of the screw).

According to the invention, this object is achieved by a housing and by a corresponding locking element, and also by a connection of such a housing to such a locking element. It should be noted here that, in such a connection, when viewed in the direction of the longitudinal axis of the housing, the housing can also be of cylindrical configuration, at least in the region of the widening recess. While the range of possible applications is in principle very wide, one application of particular importance lies, as has already been mentioned at the outset, in the provision of bone plates in which such housings are provided in one or more plate apertures, and also in the provision of corresponding bone screws as locking elements, and, finally, in the provision of corresponding sets of bone plates and bone screws.

In particular, in the housing according to the invention, the peripheral inner wall, viewed in the direction of the longitudinal axis of the housing, is approximately spherical, parabolic, elliptical or hyperbolic, at least in the region of the recess. This permits tilting of the longitudinal axis of the locking part of the locking element whose peripheral outer surface is accordingly made at least approximately spherical, at least in the region of the associated clamping surface, relative to the longitudinal axis of the housing. The longitudinal axis of the locking part of the locking element and the longitudinal axis of the housing can therefore enclose an angle. Reliable locking is nevertheless possible even at this angle, preventing automatic release of the locking part and thus of the locking element, but which locking can, if so required, be released again without damaging the housing and/or the locking element (or the locking part thereof). The locking part can be tilted in a stepless manner and can be reliably locked again at the specific tilt. It is also advantageous that the housing and the locking part in each case represent a single component. Thus, the housing can be provided directly, for example, in a plate aperture of a bone plate, and the locking part can be formed directly on the screw head of a bone screw, so that, apart from the bone plate which is needed anyway and the bone screw which is needed anyway, no further components are necessary.

In an advantageous illustrative embodiment of the housing, the recess can be arranged such that it extends in a direction perpendicular to the longitudinal axis of the housing (e.g. horizontally). In another advantageous illustrative embodiment, the recess can be arranged such that it extends in the manner of a spatial spiral round the longitudinal axis of the housing.

In an advantageous illustrative embodiment of the housing, the peripheral inner wall can have three recesses which are distributed uniformly along its circumference and which each widen outward in a wedge shape from the longitudinal axis of the housing. These three recesses (offset by 120° relative to one another) provide for uniform loading of the housing and also of the associated locking part ("tripod" principle).

A particularly advantageous embodiment may be one in which the at least approximately spherical contour of the inner wall in the direction of the longitudinal axis is described, in the region of the recess or recesses widening outward in a wedge shape from the longitudinal axis of the housing, by part of a function of the type $r = a_1 + b_1\sqrt{\alpha}$ (in the case of a spatially spiral course, when viewed in the longitudinal direction, a further component $c_1 \times \alpha$ also applies) where r is the respective distance of the inner wall from the longitudinal axis of the housing, $a_1$ and $b_1$ are constant in the plane and $c_1$ is a constant in the longitudinal direction, and $\alpha$ stands for the respective angle of revolution. This type of function describes a contour in which the respective distance r of a point on the inner wall from the longitudinal axis is obtained from a constant distance $a_1$ from the longitudinal axis plus a distance $b_1\sqrt{\alpha}$, that is to say plus a distance which, following a root function, increases depending on the angle of revolution (otherwise this region would not widen in the direction away from the longitudinal axis). In a spatial course, a component in the longitudinal direction is also superposed on this course. With such a contour, and with correspondingly suitable parameters $a_1$ and $b_1$ (or $c_1$), reliable locking is obtained, on the one hand, while, on the other hand, the connection can also be released again without causing damage.

Alternatively, the contour of the inner wall, at least approximately spherical when viewed in the direction of the longitudinal axis, can be described, in the region of the recess or recesses widening outward in a wedge shape from the longitudinal axis of the housing, by part of a logarithmic spiral, by part of a circular trajectory, by part of an involute or the like. A contour of this kind also permits reliable locking, on the one hand, while, on the other hand, the locking can also be released again without causing damage.

In a further illustrative embodiment of the housing, the latter can have, on its peripheral inner wall, a runout contour which adjoins the recess or recesses in the circumferential direction and is used for guiding the locking element out of the housing. This runout contour serves for more convenient removal of the locking element (e.g. the screw) from the housing (e.g. the plate aperture). In the case of small parts in particular (e.g. small screws), this can make handling very much easier.

In a further illustrative embodiment of the housing, the latter is provided with a countersink for receiving a screw head with a spherical underside. This also makes it possible, for example, to use bone screws with a spherical underside, but without locking contour, which are customary in the already mentioned field of osteosynthesis. The head of such a screw is then received in the customary manner by the countersink.

As has already been mentioned, osteosynthesis is a field of application of particular importance. Therefore, the invention also relates to a bone plate with plate apertures, at least one plate aperture being provided with a housing for a locking element which is to be locked with the bone plate, for example for a bone screw, for a drill guide or for a fixing pin. The housing in the plate aperture is designed as described above.

At least one plate aperture can be designed as an oblong hole in which a housing as described above is formed. This permits use of the bone plate in compression osteosynthesis and at the same time affords the advantages of the locking according to the invention.

In the locking element according to the invention, the peripheral outer surface, viewed in the direction of the longitudinal axis, is at least approximately spherical, parabolic, elliptical or hyperbolic, at least in the region of the clamping surface. This permits tilting of the longitudinal axis of the locking part of the locking element relative to the longitudinal axis of the housing (the two axes enclose an angle). Locking of the locking element is then even possible when the housing is cylindrical, in the region of the recess, instead of being at least approximately spherical, parabolic, elliptical or hyperbolic. Thus, even at an angle, it is possible to achieve reliable locking which avoids automatic loosening of the locking part and thus of the locking element, but which, when so required, can also be released again without damaging the housing and/or the locking element (or its locking part). Moreover, in the locking element, the peripheral outer surface can have three clamping surfaces which are distributed uniformly along its circumference and which each widen outward in a wedge shape from the longitudinal axis. These three clamping surfaces (offset by 120° relative to one another) permit uniform loading of the locking part of the locking element and also of the housing of the associated locking part ("tripod" principle, see above).

In the locking element according to the invention, the contour of the outer surface, in the region of the clamping surface or clamping surfaces widening outward in a wedge shape from the longitudinal axis, can be described in an azimuth plane by a function of the type $r = a_2 + b_2\sqrt{\alpha}$, where r is the respective distance of the clamping surface from the longitudinal axis, $a_2$ and $b_2$ are constants, and $\alpha$ stands for the respective azimuth angle. The advantages of such a contour, following a root function, have already been discussed above.

Alternatively, in the locking element too, the contour of the outer surface, in the region of the clamping surface or clamping surfaces widening outward in a wedge shape from the longitudinal axis, can be described in an azimuth plane by part of a logarithmic spiral, by part of a circular trajectory, by part of an involute or the like. The advantages of such a contour have also already been described above.

At least the clamping surface (but also the complete outer surface of the locking part of the locking element) can, in one illustrative embodiment, be provided with a structure. Such a (fine) structure can further improve the locking.

As has also already been mentioned, an application of particular importance is one in which the locking element is a screw, in particular a bone screw. The latter is provided with a screw shank which for its part is provided at least partially with a thread, and with a screw head which protrudes outward above the shank and the thread. The screw head here corresponds to the locking part of the locking element, as has been described above.

In this screw, at least one, but preferably four groove-like depressions can be provided in the clamping surfaces, which depressions extend substantially in the same direction and have substantially the same pitch as the thread protruding outward from the screw shank. Provision of these depressions means it is possible to avoid undesired clamping of the screw head, as could occur in very unfavorable circumstances as a result of the clamping surface being clamped by an inwardly projecting region of the contour of the housing. An inwardly projecting region of this kind can, in such circumstances, slide into a groove-like depression and, upon further screwing-in of the screw, is channeled through by the groove-like depressions, by virtue of the course and pitch of said groove-like depressions. After this, the screw runs free again, i.e. for a short time there is no contact between housing and screw head. Upon further screwing, the locking action already described above then sets in. Despite the presence of the groove-like depressions, a sufficiently large clamping surface remains to ensure reliable blocking of the screw head in the housing of the bone plate.

Also of particular importance, finally, is a set of bone plates and bone screws, containing at least one bone plate, as described above, and at least one bone screw (preferably several bone screws), as described above. These sets are regularly used in connection with the treatment of fractures.

As has already been mentioned above, another important aspect of the invention is the connection of a housing, as described above, to a locking element, as described above.

The housing, viewed in the direction of the longitudinal axis of the housing, can be cylindrical, at least in the region of the recess, instead of being approximately spherical, parabolic, elliptical or hyperbolic. This likewise permits reliable locking, while, on the other hand, the connection can also be released again without damage, when so required.

Such a connection also has a particular field of application in osteosynthesis. Therefore, the invention also relates to a connection of a bone plate, as described above, to a screw, as described above.

Further advantageous configurations of the invention will become clear from the following description of illustrative embodiments of the invention with reference to the schematic drawing, in which.

DETAILED DESCRIPTION

The explanations given below relate to the specific field of application of bone screws and bone plates. As has already been mentioned above, this is a field of application of particular importance. However, the invention is not restricted to this field of application and instead relates quite generally to connections of the kind explained below with reference to the illustrative embodiment of bone screws and bone plates.

In addition, only illustrative embodiments are explained below in which both the housing of the bone plate in the region of the recess and also the clamping surface on the screw head are of spherical configuration when viewed in the direction of the longitudinal axis. The recess can, however, also be approximately parabolic, elliptical or hyperbolic, for example. This also applies to the clamping surface. The recess can even be cylindrical and, together with an approximately spherical, parabolic, elliptical or hyperbolic clamping surface, can form a connection in which suitable locking takes place.

Figure 1:
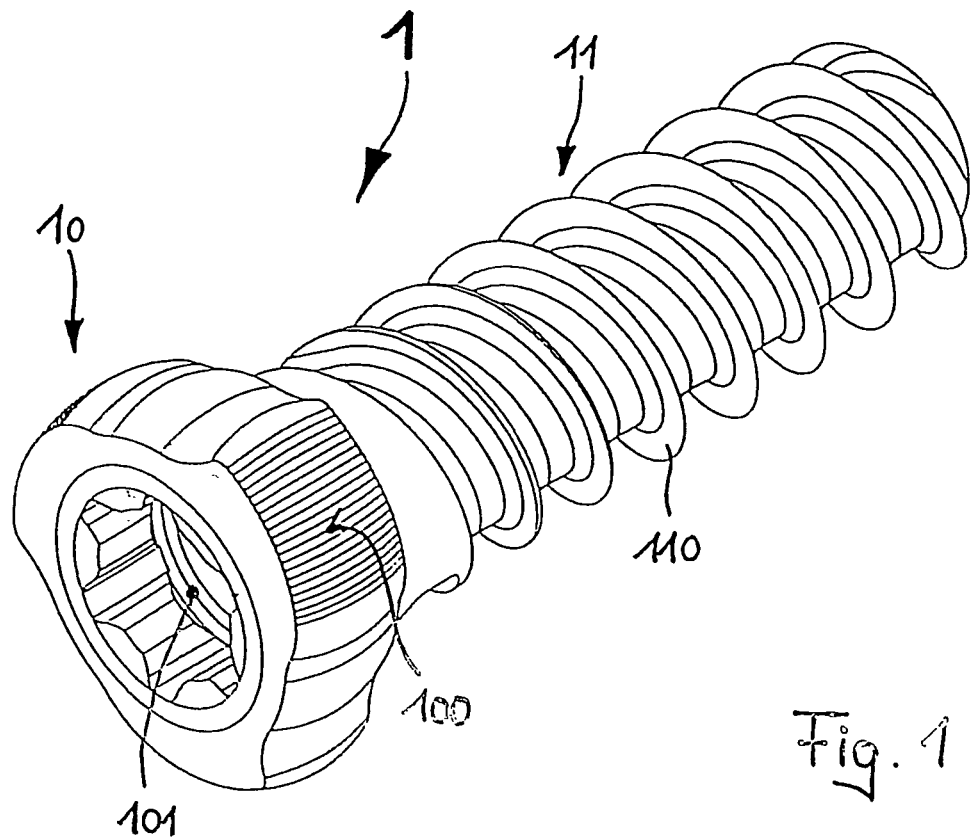
FIG. 1 shows a perspective view of an illustrative embodiment of a locking element according to the invention in the form of a bone screw.

FIG. 1 shows an illustrative embodiment of a locking element according to the invention in the form of a bone screw 1. The locking part of the bone screw 1 is here formed by the screw head 10. This screw head 10 has a different design than a screw head of a conventional bone screw (that is to say it is not round). In particular, it has clamping surfaces 100, and in the illustrative embodiment shown here there are three of these clamping surfaces 100 arranged uniformly along the circumference of the outer surface of the screw head 10. Viewed in an azimuth plane, that is to say in a plane perpendicular to the longitudinal axis of the screw 1, these clamping surfaces 100 widen outward in a wedge shape in order to effect locking (wedging) of the screw 1 in a corresponding housing of a bone plate.

In the screw head 10 in FIG. 1, a tool socket 101 can also be seen which is suitable for receiving a tool (not shown) for turning the screw 1 in or out. The screw shank 11 is provided with a shank thread 110 which serves to turn the screw 1 into the bone. The shank thread 110 can be designed, for example, as a self-tapping thread.

Figure 2:
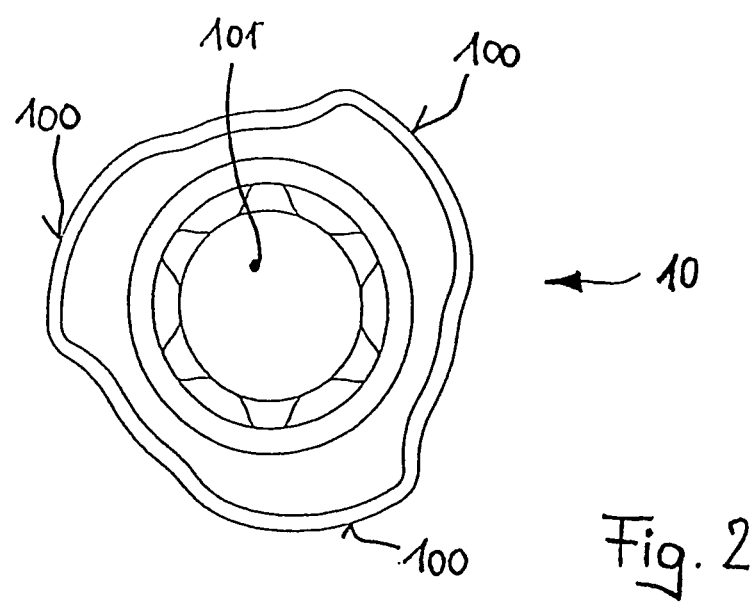
FIG. 2 shows a plan view of the bone screw from FIG. 1.

The outer surface of the screw head is at least approximately spherical, at least in the region of the clamping surface 100, but here in other regions too, when viewed in the longitudinal direction of the screw 1. This aspect will be dealt with in greater detail below when discussing the locking of the screw in a housing. In the plan view in FIG. 2, this at least approximately spherical contour in the longitudinal direction can be seen from the fact that, in addition to the boundary of the outer surface extending in the longitudinal direction of the screw 1 at the upper end of the screw head (inner line), it is also possible to discern the most outwardly protruding part of this outer surface (outer line).

In an azimuth plane, that is to say in a plane perpendicular to the longitudinal axis of the screw 1, the contour of the clamping surface 100 widening outward in a wedge shape can be described, for example, by a function of the type $r = a_1 + b_1 \sqrt{\alpha}$ (in this connection see also FIG. 5), that is to say by a "root function". Here, r is the distance of the clamping surface from the longitudinal axis, $a_1$ and $b_1$ are constants, and $\alpha$ stands for the respective azimuth angle. Viewed in the azimuth plane, the clamping surface 100 can also be described by part of a logarithmic spiral. Other describing functions can in principle also be considered.

Figure 3:
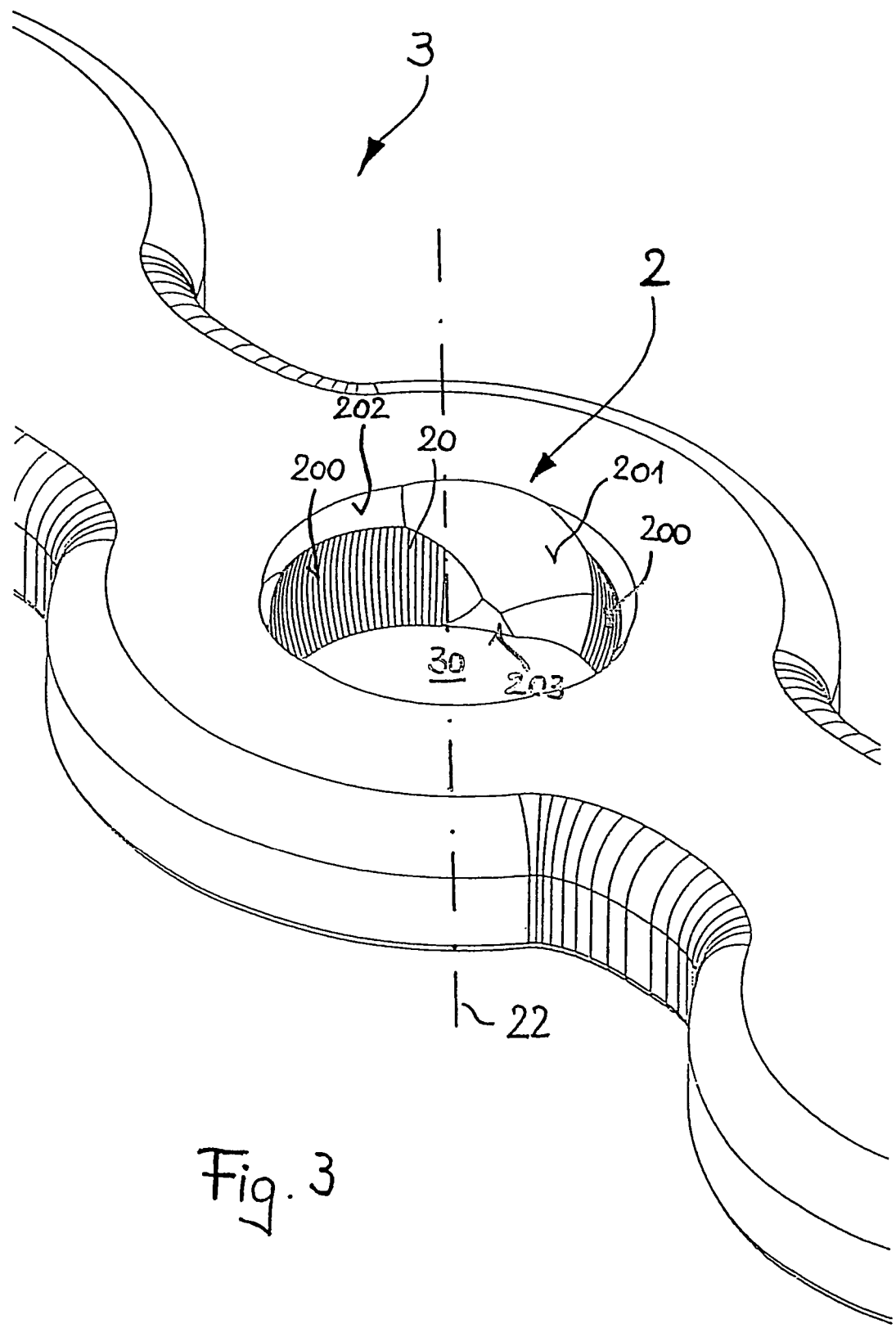
FIG. 3 shows a perspective view of a detail from a bone plate, with an illustrative embodiment of a housing according to the invention in the plate aperture.
Figure 4:
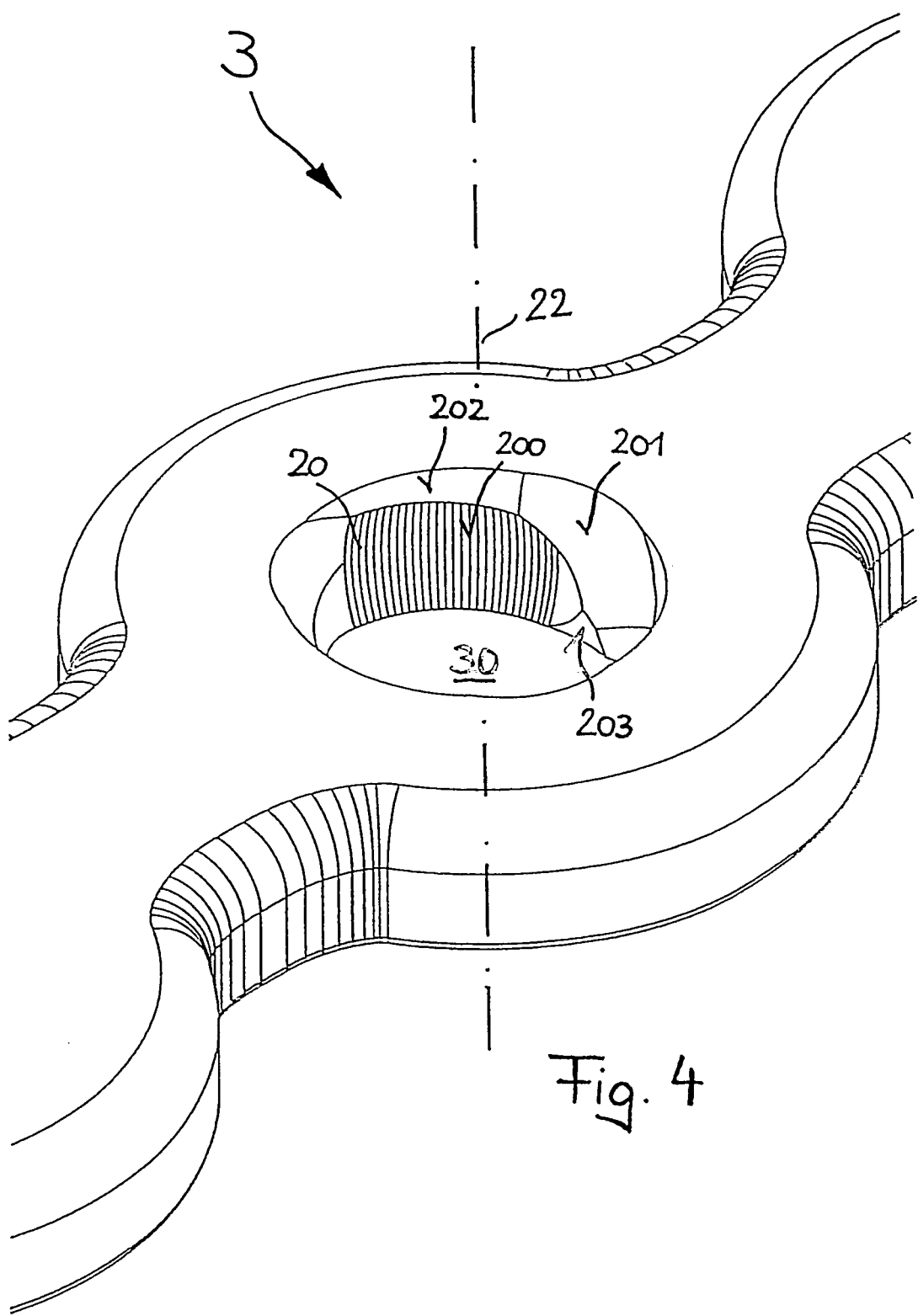
FIG. 4 shows the detail of the bone plate from FIG. 3 in another perspective view.

FIG. 3 and FIG. 4 in each case show a perspective view of a detail from a bone plate 3. The plate aperture 30 of the bone plate 3 is provided with a housing 2 which can receive a locking part of a locking element, that is to say, for example, the screw head 10 of the bone screw 1. In the illustrative embodiment shown, the housing 2 has, on its inner peripheral wall, three recesses 20 which are distributed uniformly along the circumference and in which the inner wall 200, viewed in an azimuth plane, that is to say in a plane perpendicular to the longitudinal axis 22 of the housing, widens outward in a wedge shape from the longitudinal axis of the housing 2 (here identical to the plate aperture axis). The longitudinal axis 22 here extends perpendicular to the plane of the plate, although in principle the longitudinal axis could also be set at another angle to the plane of the plate (oblique plate aperture with housing).

On the peripheral inner wall it is also possible to see a runout contour 201 which adjoins the inner wall 200 widening in a wedge shape in the region of the recess 20. This runout contour 201 serves for guiding the screw 1 out, making it easier to remove the latter from the housing 2.

A countersink 202 can also be seen which is used to receive a screw head, with spherical underside, of a conventional bone screw, that is to say a bone screw in which the screw head is not locked with the housing in the plate aperture of the bone plate.

The region 203 of the inner wall of the housing 20 results from the cylindrical core bore of the plate aperture 30, which bore is produced first, before the other regions are produced by milling (region 200) or drilling (region 203) and countersinking (region 202).

Figure 5:
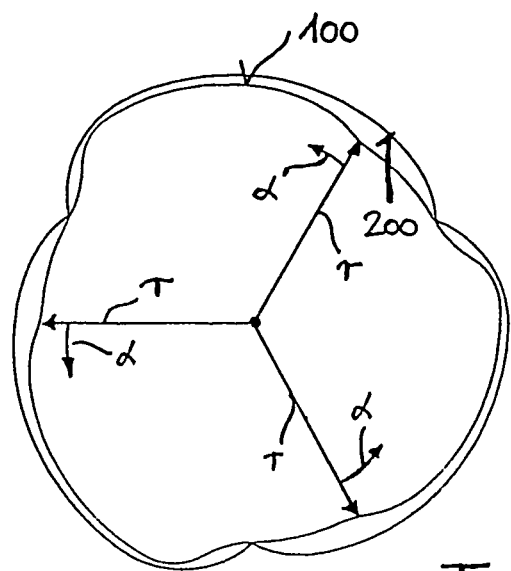
FIG. 5 shows a schematic representation of the outer contour of the screw head and of the corresponding inner contour of the housing, in the unlocked position.
Figure 6:
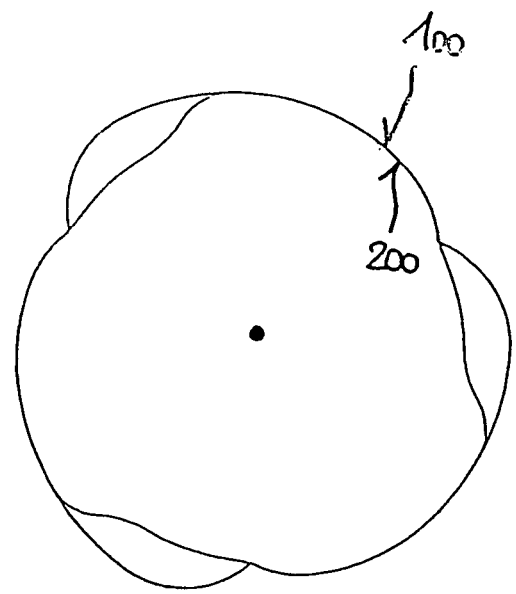
FIG. 6 shows the representation according to FIG. 5, but in the locked position.

FIG. 5 and FIG. 6 each show a schematic representation of the outer contour of the screw head and of the corresponding inner contour of the housing in an azimuth plane, on the one hand in the unlocked position (FIG. 5) and on the other hand in the locked position (FIG. 6). This also shows somewhat more clearly that the outer contour of the clamping surface 100 of the screw head 10 can be described in an azimuth plane, for example, by the aforementioned "root function", FIG. 5 in particular showing in each case the radius r at the start of the outer contour described by the "root function", and also the azimuth angle $\alpha$. The surface 200 of the recess 20 of the housing, which surface 200 likewise widens in this case in accordance with a "root function", can also be seen here. If the screw head is turned clockwise relative to the housing, the screw head is then locked in the housing, resulting in the situation shown in FIG. 6. The screw (or, to be more exact, the screw head) and the bone plate are connected fixedly to one another.

Figure 7:
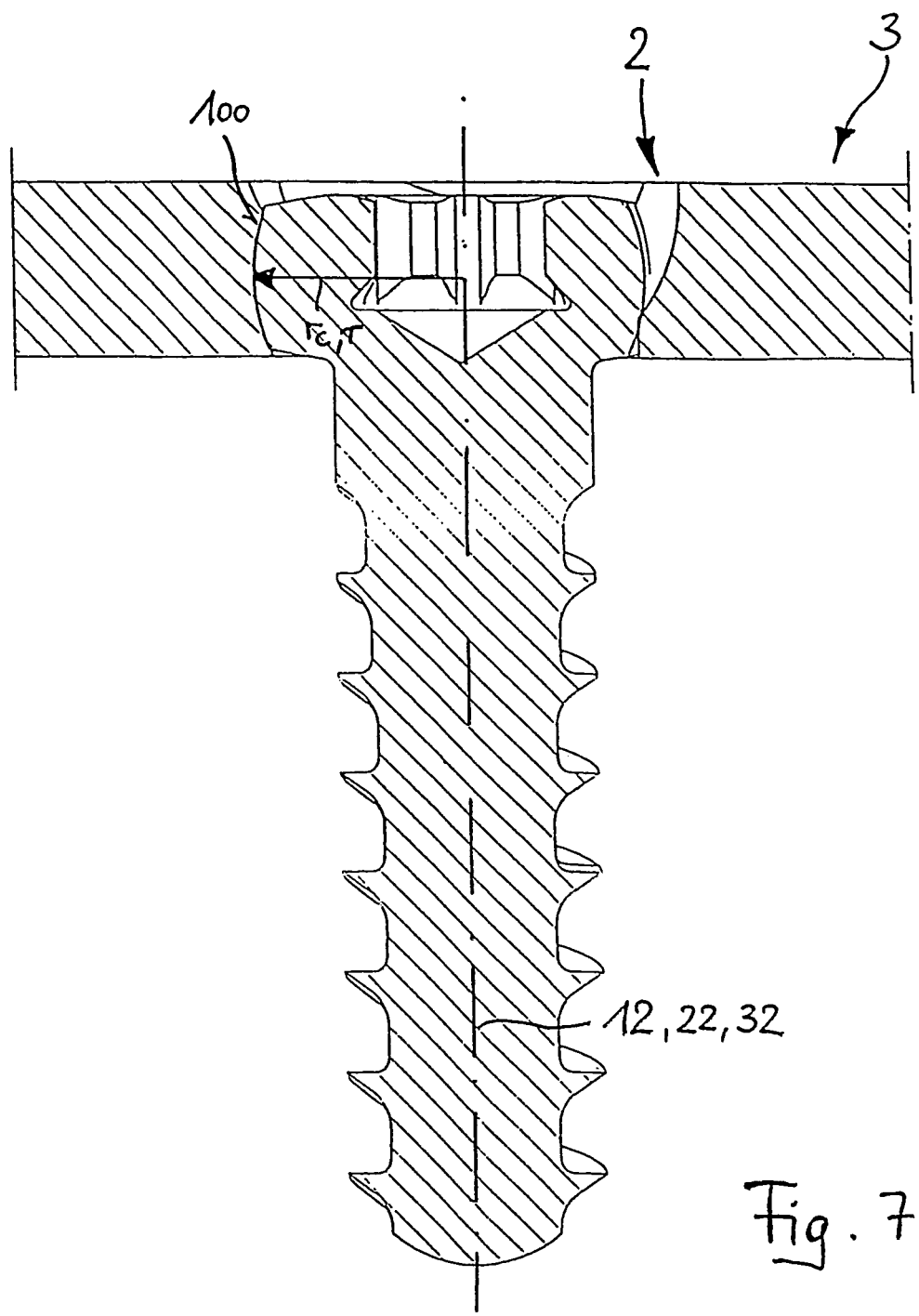
FIG. 7 shows a sectional view of a screw arranged in the plate aperture of a bone plate, the longitudinal axis of the screw coinciding with the longitudinal axis of the plate aperture.
Figure 8:
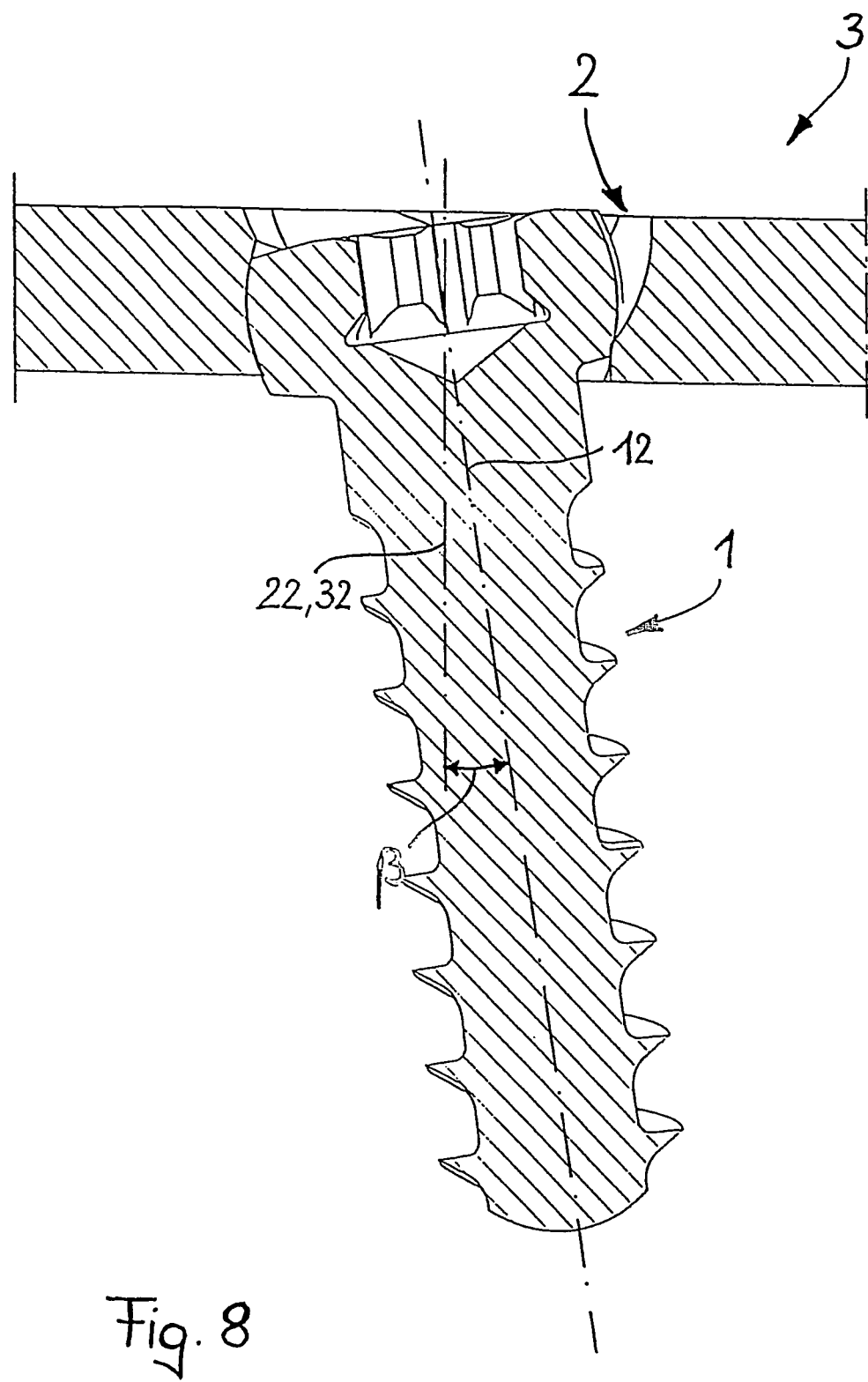
FIG. 8 shows the view of the screw in the plate aperture from FIG. 7, the longitudinal axis of the screw and the longitudinal axis of the plate aperture enclosing an angle.

FIG. 7 shows, in longitudinal section, a bone screw 1 locked in the housing 2 (corresponding to the situation in FIG. 6). Here, the longitudinal axis 12 of the screw 1 coincides with the longitudinal axis 32 of the plate aperture of the bone plate 3 and also with the longitudinal axis 22 of the housing, so that the longitudinal axis of the screw and the longitudinal axis of the plate aperture and of the housing do not enclose an angle with one another. It will also be seen from FIG. 7 that the radius of curvature $r_c$ of the clamping surface 100, which is spherical when viewed in the longitudinal direction, has its foot on the longitudinal axis 12 of the screw 1, analogous considerations applying to the recess. This means that the ratio of the radius of curvature $r_c$ to the actual distance r (see FIG. 5) of the point on the clamping surface from the longitudinal axis 12 of the screw here amounts exactly to 1. However, since the radius of curvature $r_c$ is constant, but the actual distance r of a point, by contrast, changes in the circumferential direction in the region of the clamping surface (the clamping surface, like the recess too, widens outward from the longitudinal axis 12 or 22), this cannot apply across the entire region of the clamping surface or recess. On the other hand, the radius of curvature $r_c$ must lie within certain limits in order to permit tilting of the screw, on the one hand, and secure locking of the screw, on the other hand. In this connection, an expedient ratio of the radius of curvature $r_c$ to the distance r of the point on the clamping surface of the screw, or the inner wall of the recess, from the longitudinal axis 12 or 22, respectively, lies in the range of from 0.3 to 3, this ratio preferably being approximately 1. This applies equally to the inner wall of the recess as to the outer wall of the screw. The position of the bone screw 1 shown in FIG. 8, and likewise locked in the housing 2, is different than in FIG. 7. Here, the longitudinal axis 32 of the plate aperture and longitudinal axis 22 of the housing enclose an angle β with the longitudinal axis 12 of the screw; the inclination of the screw 1 can be not only in the direction of the longitudinal axis of the bone plate 3, but in any desired direction. Since the screw here once again sits as it were in a ball seat, renewed locking is possible.

Figure 9:
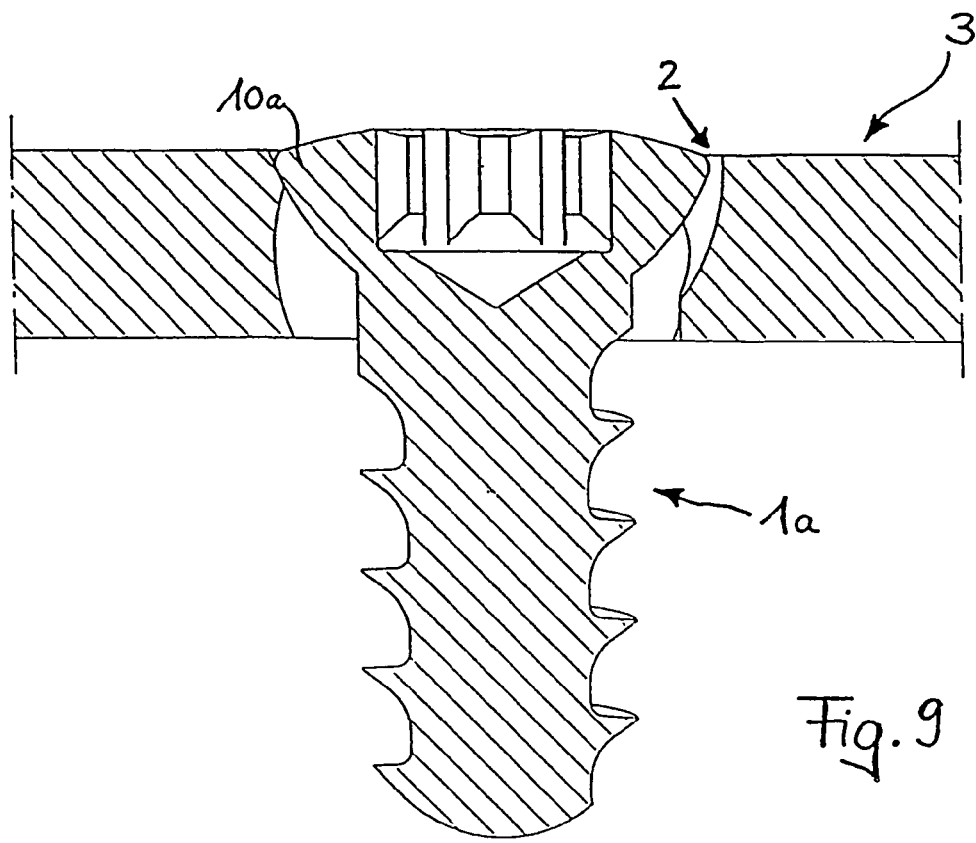
FIG. 9 shows a sectional view of a conventional bone screw with a spherical underside of the head in the plate aperture, the longitudinal axis of the screw and the longitudinal axis of the plate aperture coinciding.
Figure 10:
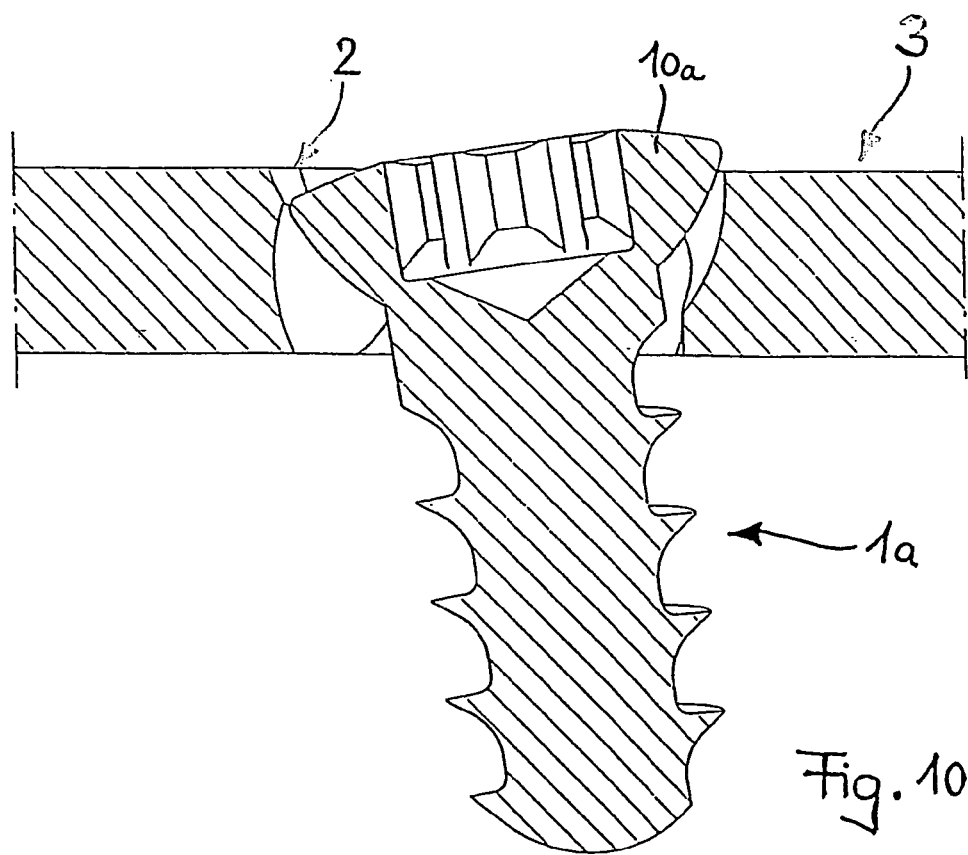
FIG. 10 shows the sectional view from FIG. 9, but with the longitudinal axis of the screw and the longitudinal axis of the plate aperture enclosing an angle.

FIG. 9 and FIG. 10 each show a bone plate 3 in which a conventional bone screw 1a whose head has a spherical underside is held straight in the housing 2 (FIG. 9) and at an angle in the housing 2 (FIG. 10). The head 10a of the screw 19 rests on the corresponding countersink 202 (see FIG. 3, FIG. 4) of the housing 2. The housing 2 can therefore also receive conventional screws 1a whose heads have a spherical underside, as a result of which the bone plate 3 can be fixed in a conventional manner by being pressed against the bone, but without the above-described locking of the screw 1a and the bone plate 3 or housing 2.

Figure 11:
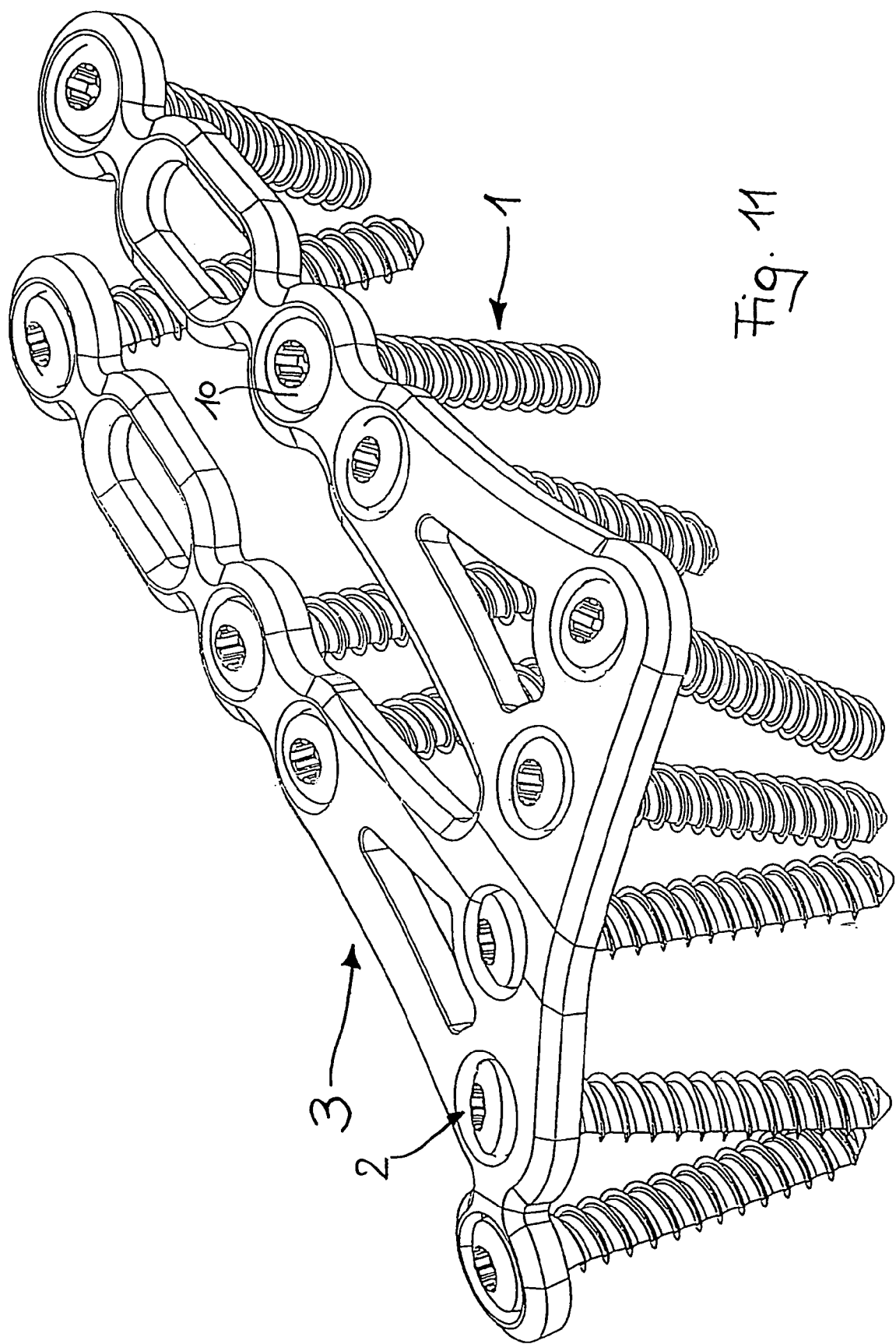
FIG. 11 shows a bone plate that can be used in the field of hand surgery, with a plurality of screws arranged in the plate apertures at different angles.

FIG. 11 shows a bone plate 3 of the kind that can be used in the field of hand surgery, with a plurality of bone screws 1 whose screw heads 10 are arranged and locked in the plate apertures at different angles in the corresponding recess 2. In the field of hand surgery in particular, it is more common for quite a large number of sometimes small bone segments to have to be fixed and positioned relative to one another with just one screw, and in this case it is also especially important that the position of an already positioned bone segment can be modified again without too much effort, in order to ensure optimal treatment.

This will be explained in somewhat greater detail below with the aid of FIGS. 12-19. For this purpose, two bone segments BS1 and BS2 are shown in greatly simplified form, and also a bone plate 3 which has already been connected to the bone segment BS1 with the aid of two screws 1. The two screws 1 connected to the bone segment BS1 are locked in the housing 2 of the bone plate 3 in the manner already explained, the orientation of the screw axis not necessarily having to be perpendicular to the bone. The description is also given with reference to plate apertures whose axis extends perpendicularly through the bone plate. However, it is also conceivable that the axis of the plate apertures and the longitudinal axis of the housing extend at an angle different than 90° through the bone plate (oblique bore), although the function principle remains essentially the same.

Figure 12:
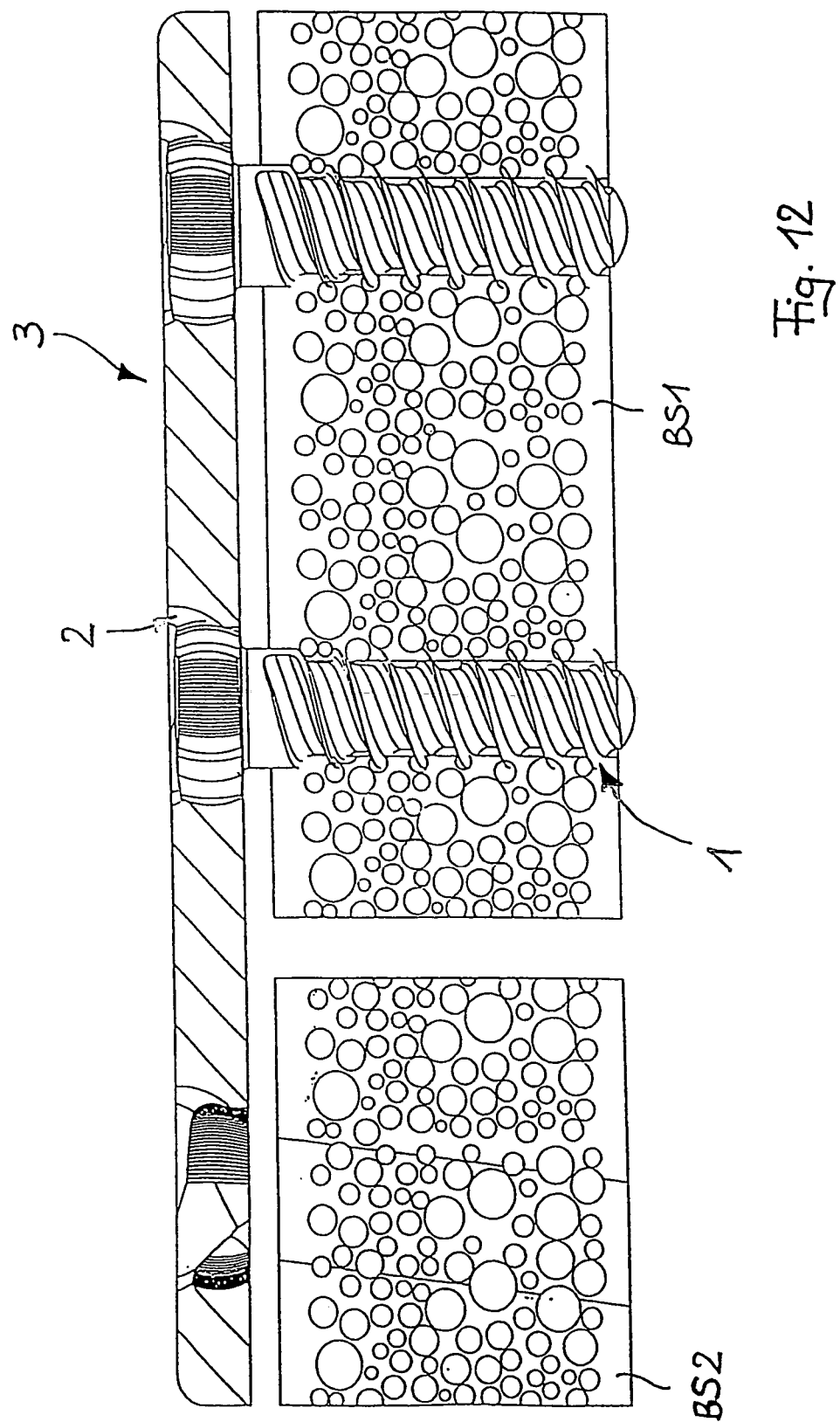
FIGS. 12 to 19 show different individual steps (alignment, fixation, etc.) in the treatment of a fracture.

In FIG. 12, no screw 1 has as yet been screwed into the bone segment BS2; only a plate aperture with a corresponding housing 2 lies over the location where a screw 1 will be screwed into the bone segment BS2. However, the figure already indicates that the screw 1 is to be introduced at an angle relative to the perpendicular.

Figure 13:
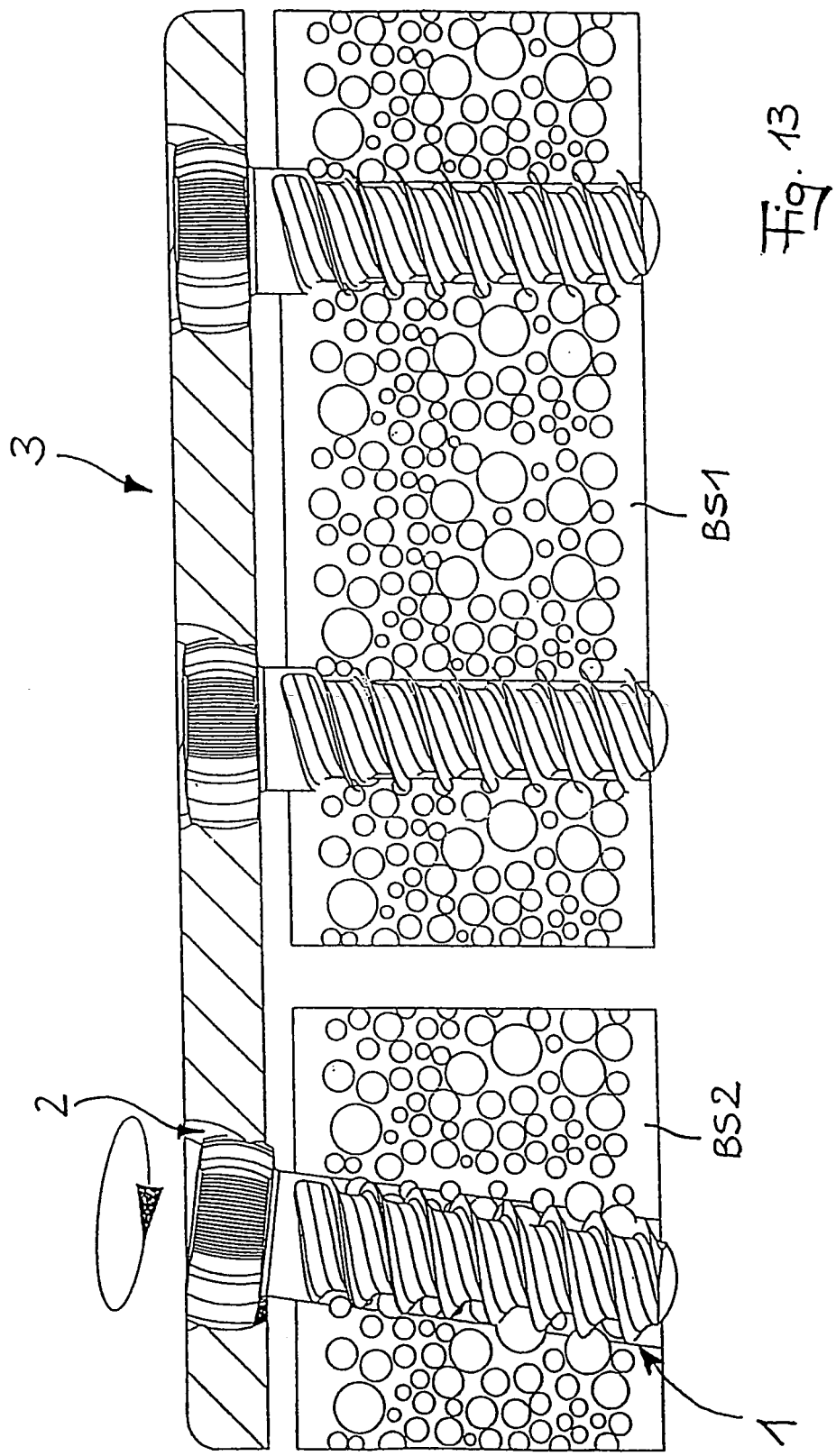
Figure 14:
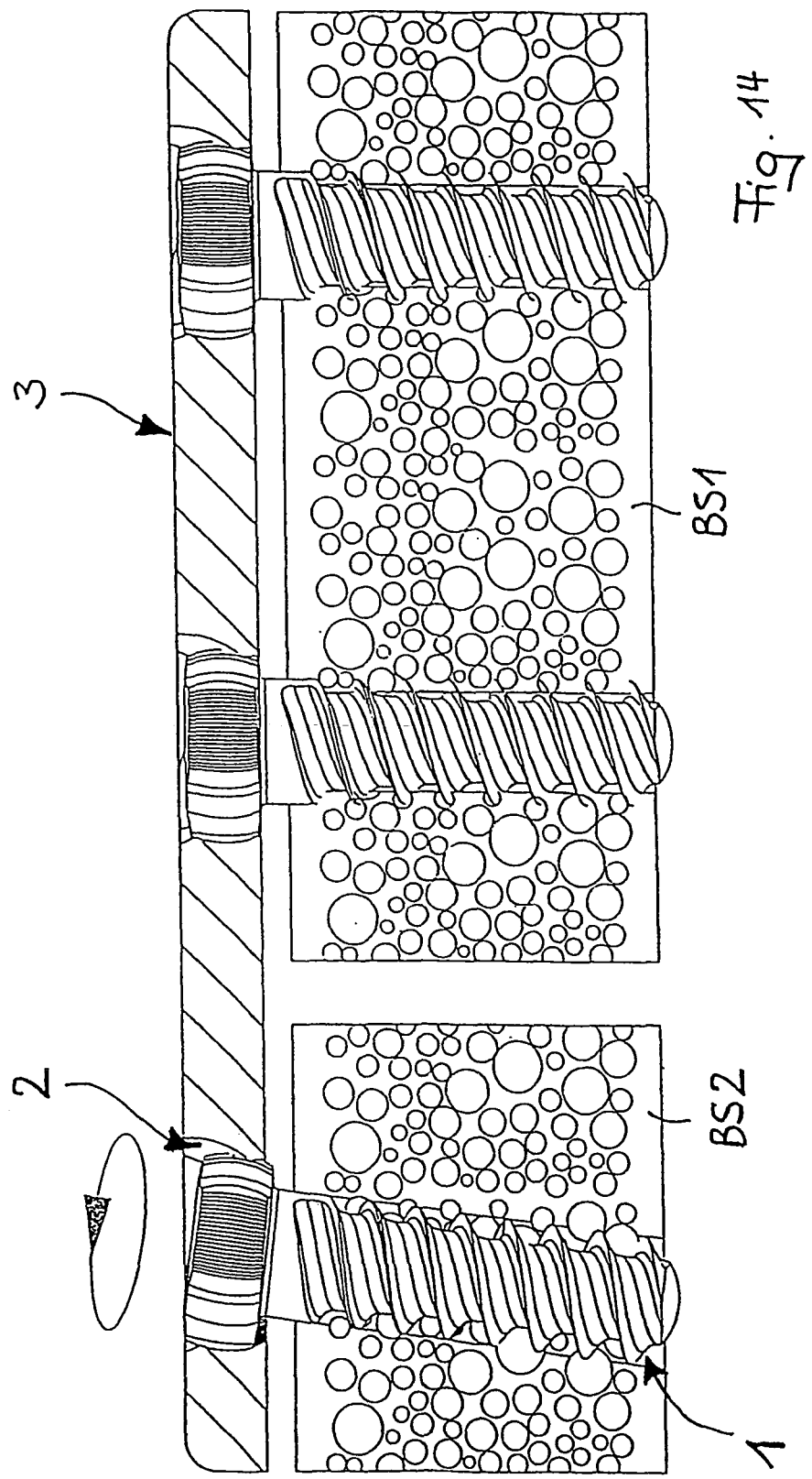

In FIG. 13, the bone screw 1 is then screwed into the bone segment BS2 and locked in the housing 2 of the bone plate 3.

For this purpose, the screw 1 is turned in the direction (clockwise) indicated by the arrow shown above the corresponding housing 2.

If the bone segment BS2 is now to be repositioned relative to the bone segment BS1, the locking of the screw 1 screwed into the bone segment BS2 must be released again. This is achieved by turning the screw 1 in the direction (counterclockwise) of the arrow shown above the corresponding housing (FIG. 14).

Figure 15:
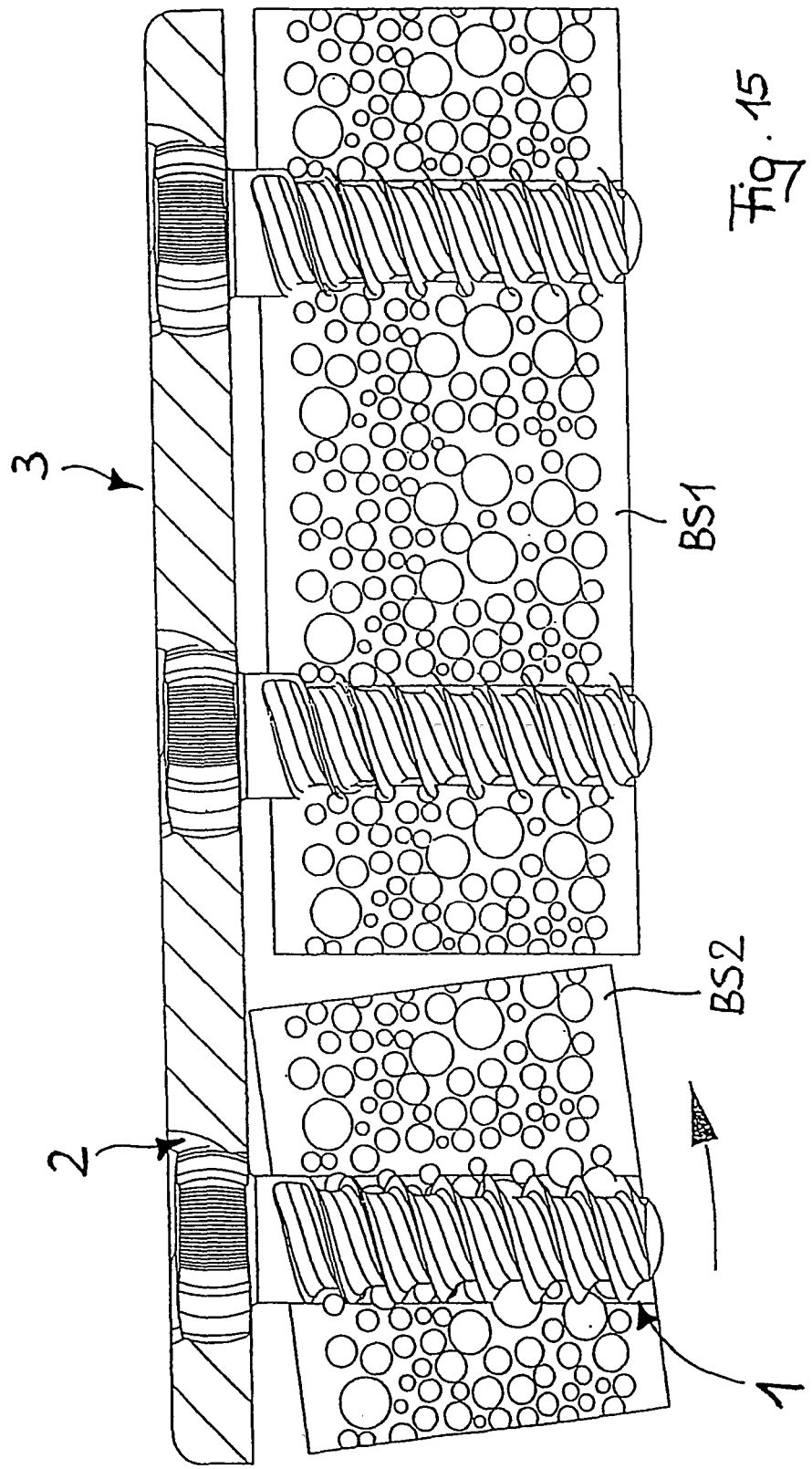
Figure 16:
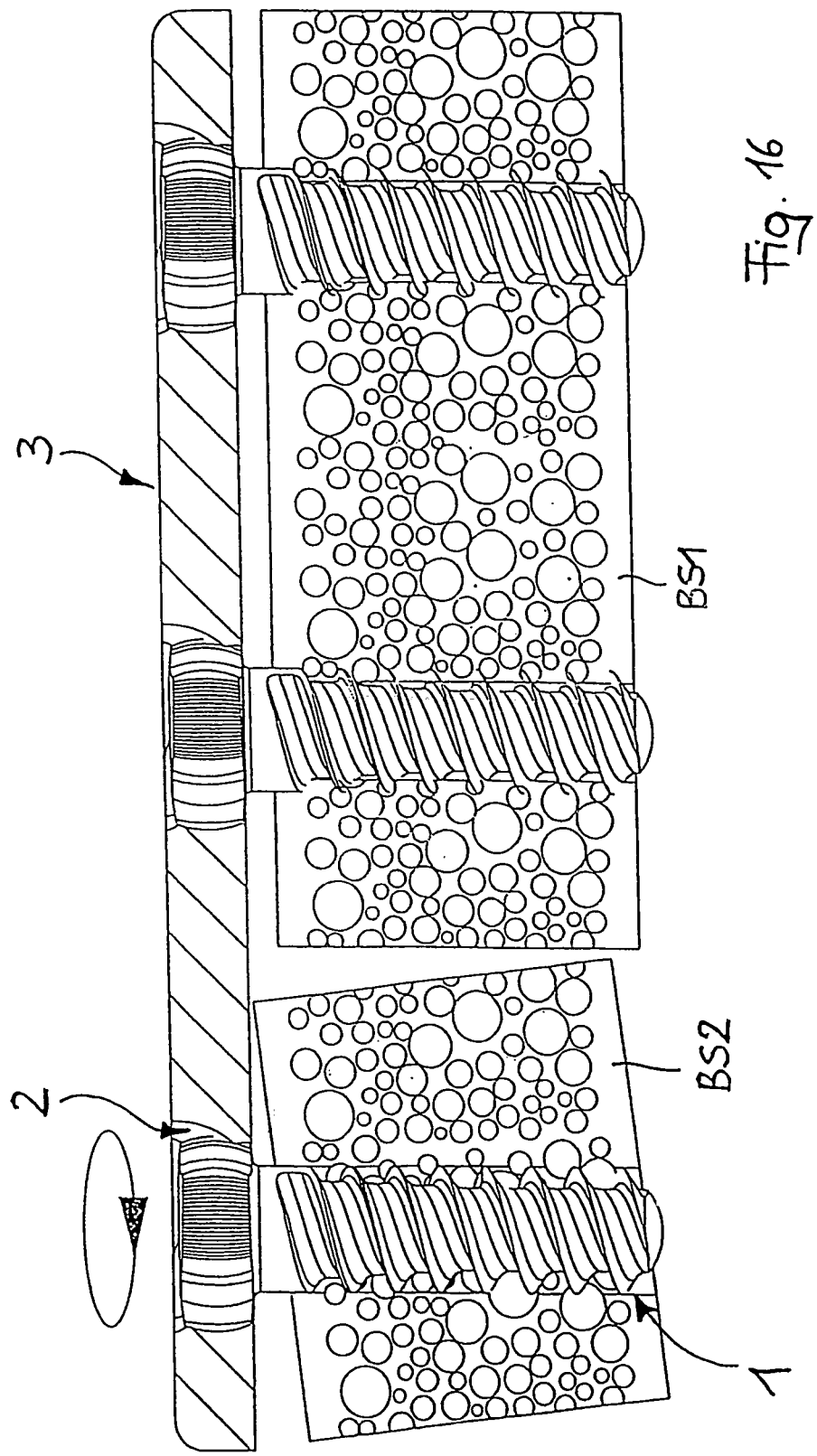
Figure 17:
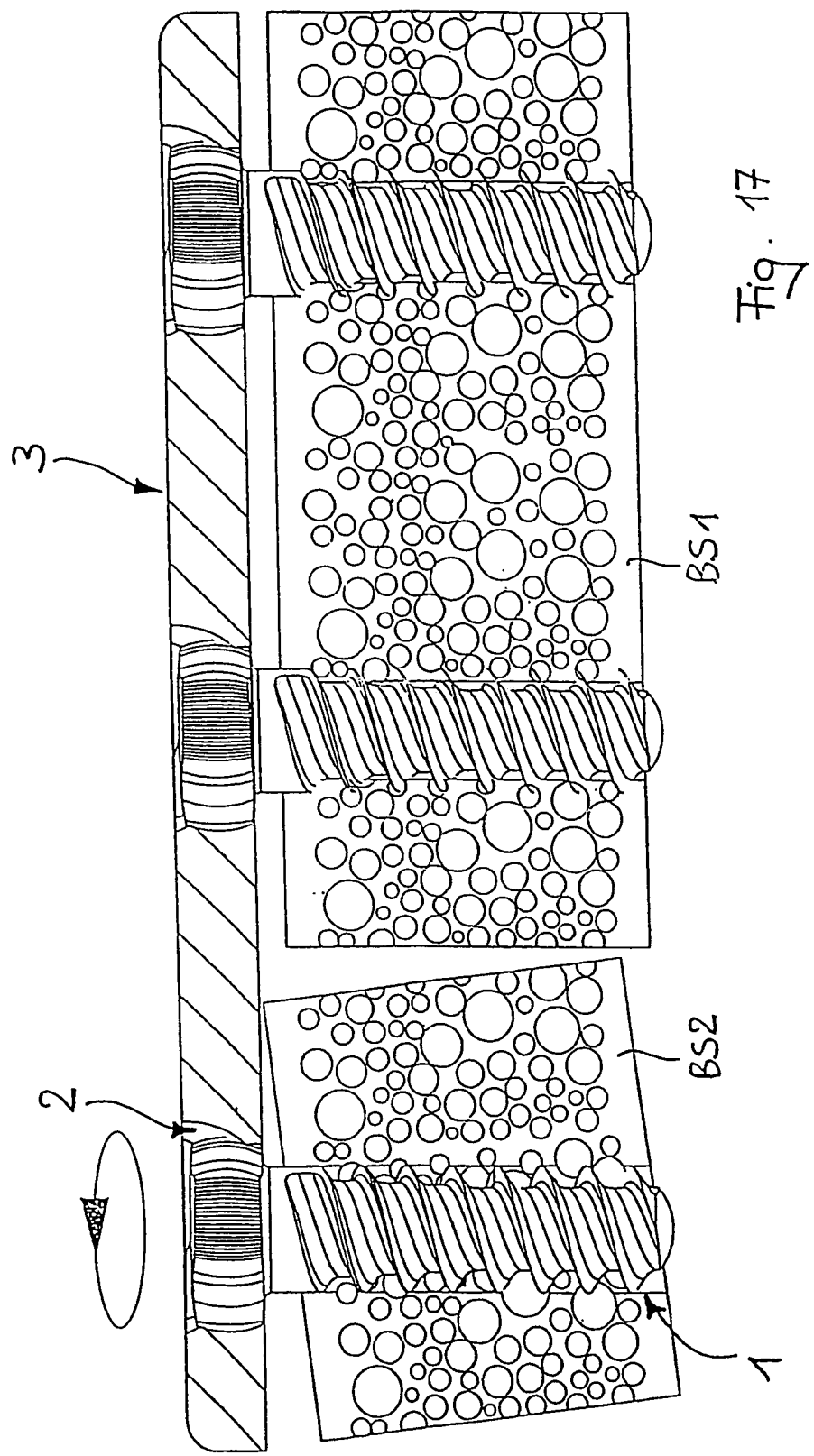

After the locking has been released, the bone segment BS2, with the screw 1 screwed into it, can for example be tilted about an angle into a desired position, as is indicated in FIG. 15 by the arrow shown below the bone segment BS2.

After the bone segment BS2 has been tilted into the new desired position, locking is repeated by turning the screw 1 in the direction (clockwise) of the arrow shown above the screw 1 in FIG. 16.

If it again transpires that the position of the bone segment BS2 is to be altered, the locking is once again released by turning the screw 1 in the direction (counterclockwise) of the arrow shown above the screw in FIG. 17.

Figure 18:
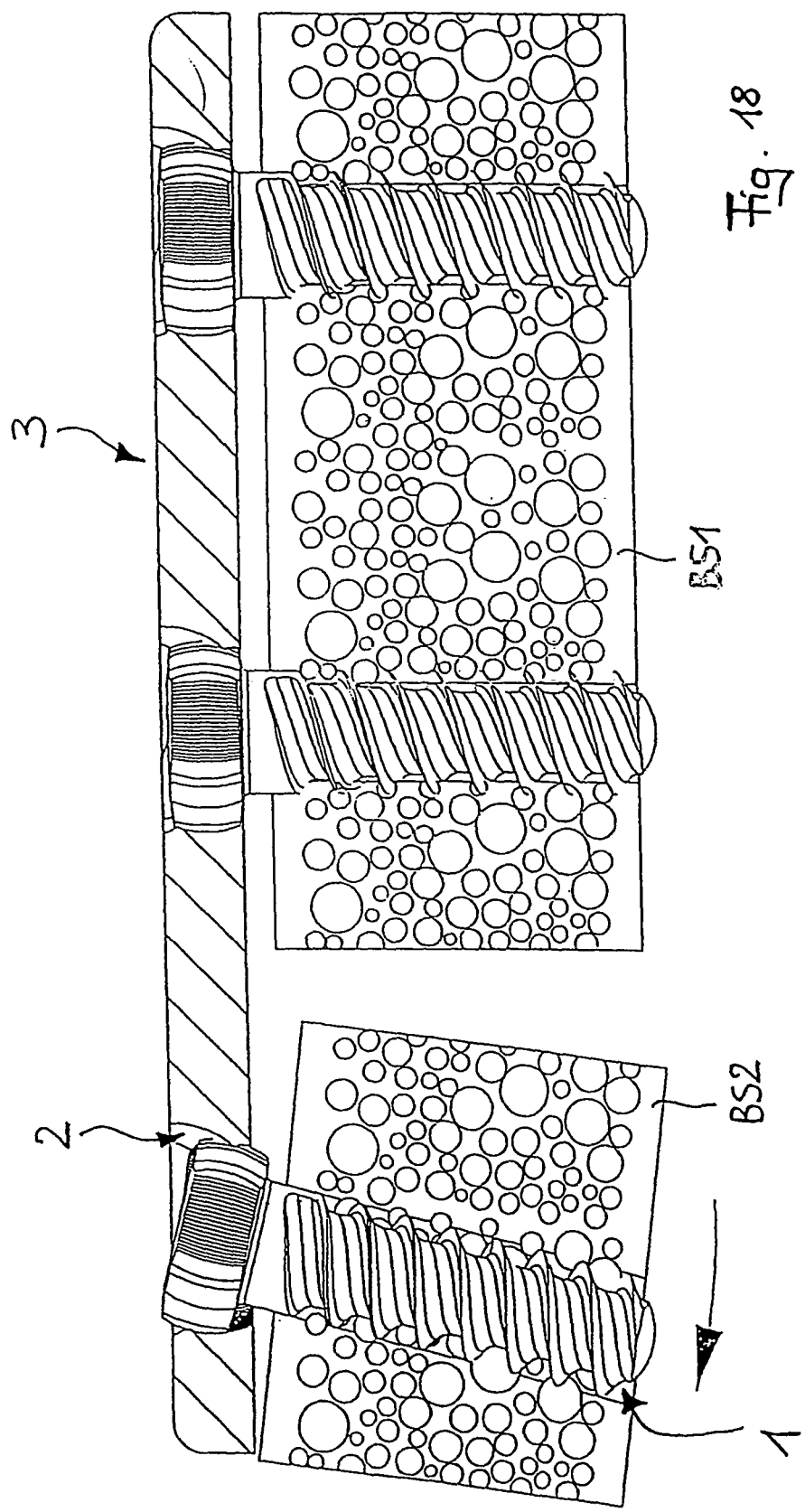

The bone segment can then be moved into the new desired position, for example tilted in the manner indicated in FIG. 18 by the arrow shown below the bone segment BS2.

Figure 19:
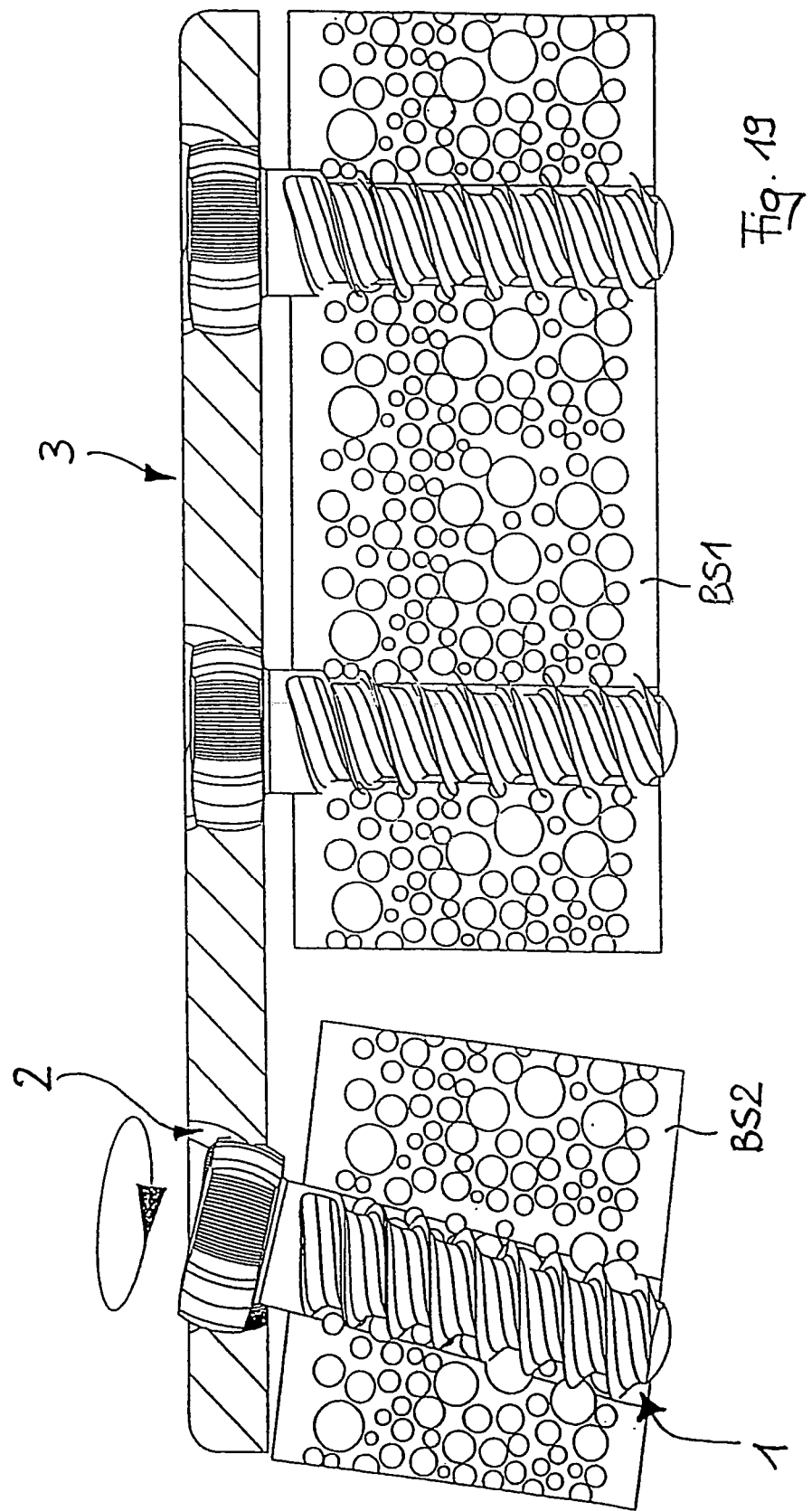

For renewed locking (fixing), the screw 1 is turned in the direction (clockwise) of the arrow shown in FIG. 19, as a result of which the position of the bone segments BS1 and BS2 relative to one another is fixed. New bone can then form over time in the fracture line.

Figure 20:
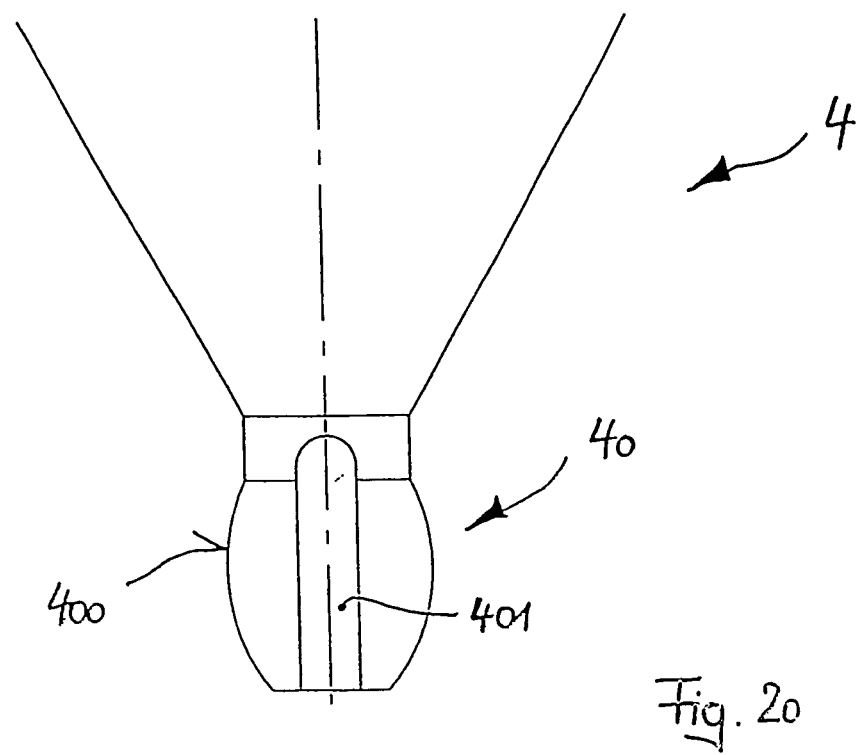
FIG. 20 shows an illustrative embodiment of a milling cutter with which the inner contour of the housing can be produced.

FIG. 20 is a schematic representation of a detail from an illustrative embodiment of a milling cutter 4 with which the inner wall 200 of the recess 20 can be produced. It will be noted that the milling cutter has a convex cutter head 40 with an at least approximately spherical contour 400 for producing the inner wall 200 of the recess 20. For this purpose, the milling cutter 4 is guided under CNC control, for example, according to the "root function" or according to the "logarithmic spiral" (or the circular trajectory, involute, etc., see above) through the region of the respective recess 20, so that the desired contour of the inner wall 200 is obtained in this area. The groove 401 provided in the cutter head 40 is used for removing the chips. Before this, a cylindrical core drill has been drilled through the bone plate 3 (core drill of the plate aperture 30), into which the milling cutter 4 can be introduced in order to then produce the corresponding contour of the inner wall 200 under CNC control.

Figure 21:
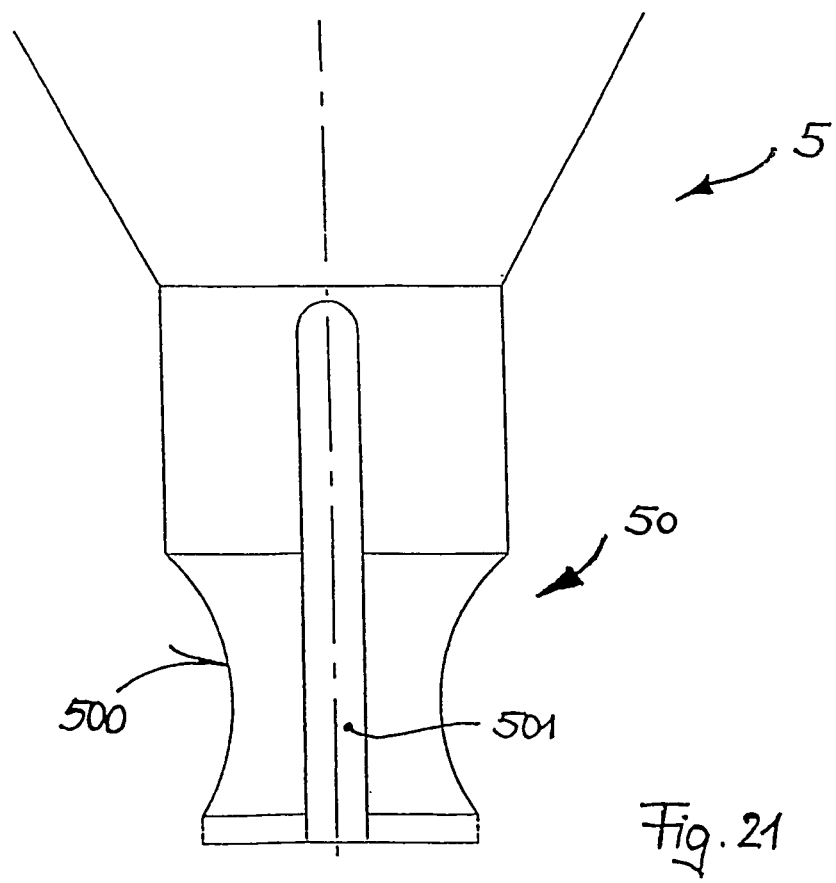
FIG. 21 shows an illustrative embodiment of a milling cutter with which it is possible to produce the outer contour of the locking element used for locking purposes.

The outer surface of the screw head 10 can be produced using a milling cutter 5 with a concave cutter head 50 which also has an at least approximately spherical contour 500, as is shown schematically in FIG. 21. The groove 501 is used for removal of chips. To produce the outer surface of the screw head 10, the milling cutter 5 is guided along a for example cylindrical screw head, for example under CNC control. In the region of the clamping surfaces 100 of the screw head 10, this can, for example, be done according to the "root function" or, for example, according to the "logarithmic spiral" (or circular trajectory, involute, etc., see above). In the regions between the clamping surfaces, this can be done according to another function, in which case it must in principle be ensured that, upon tilting of the screw, the outer surfaces of the screw head 10 do not collide with the inner wall of the housing 2 and prevent tilting. Otherwise, in the regions between the clamping surfaces 100, viewed in the longitudinal direction of the screw, the outer surface of the screw head can also be produced using the same milling cutter 5 as for the clamping surfaces 100.

Figures 22, 23:
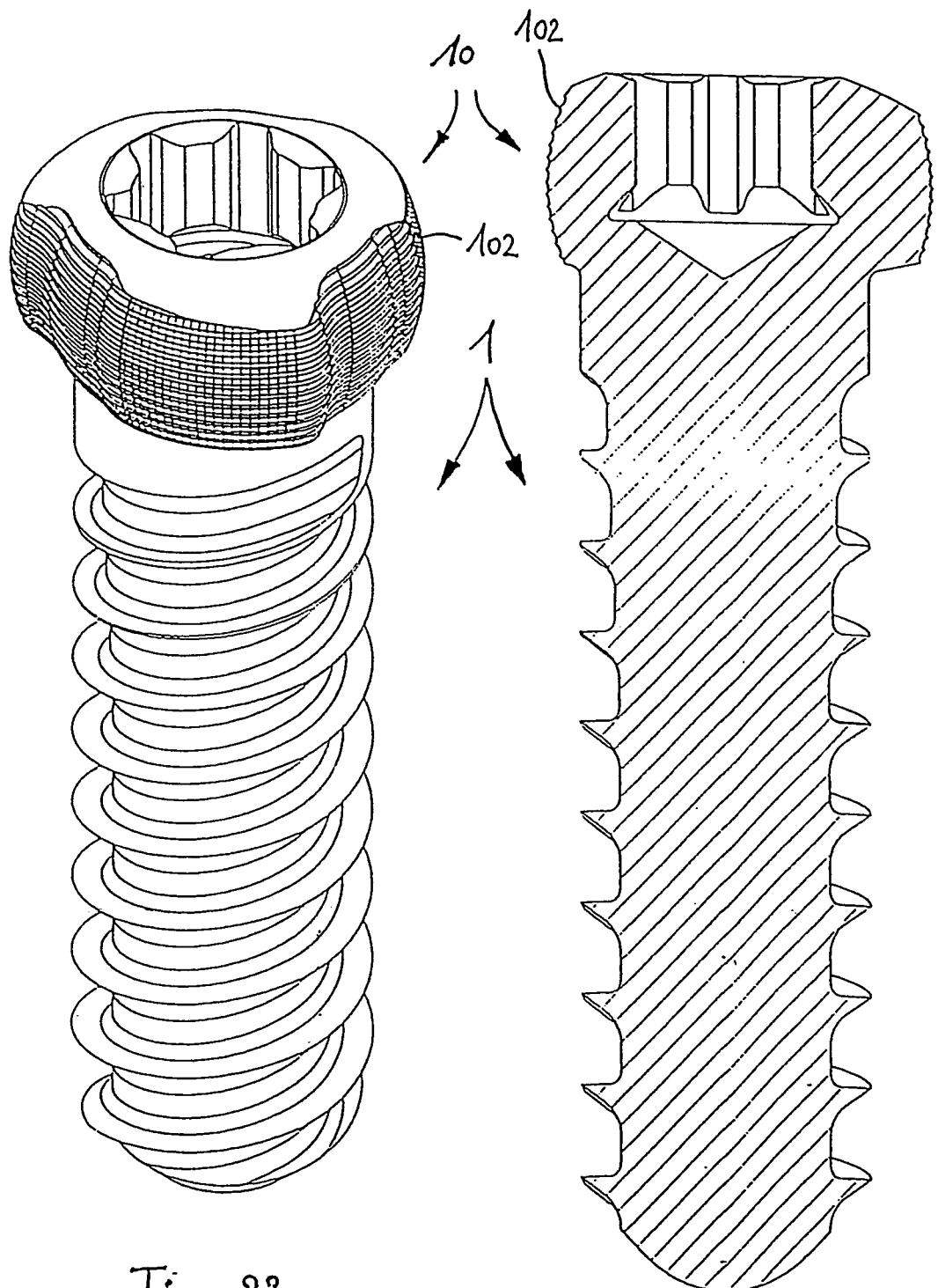
FIG. 22 shows the bone screw from FIG. 1, but with an additional surface structure on the outer wall of the screw head.
FIG. 23 shows the bone screw from FIG. 22 in longitudinal section.

FIG. 22 shows a perspective view of the screw 1, and FIG. 23 a longitudinal sectional view through the screw 1, from which it will be seen that the outer surface of the screw head 10 of the screw 1 can also be provided with a structure 102. Such an additional (fine) structure 102 (here, for example, in the form of peripheral grooves) can further improve the locking of the screw head 10 in the recess 20.

Figure 24:
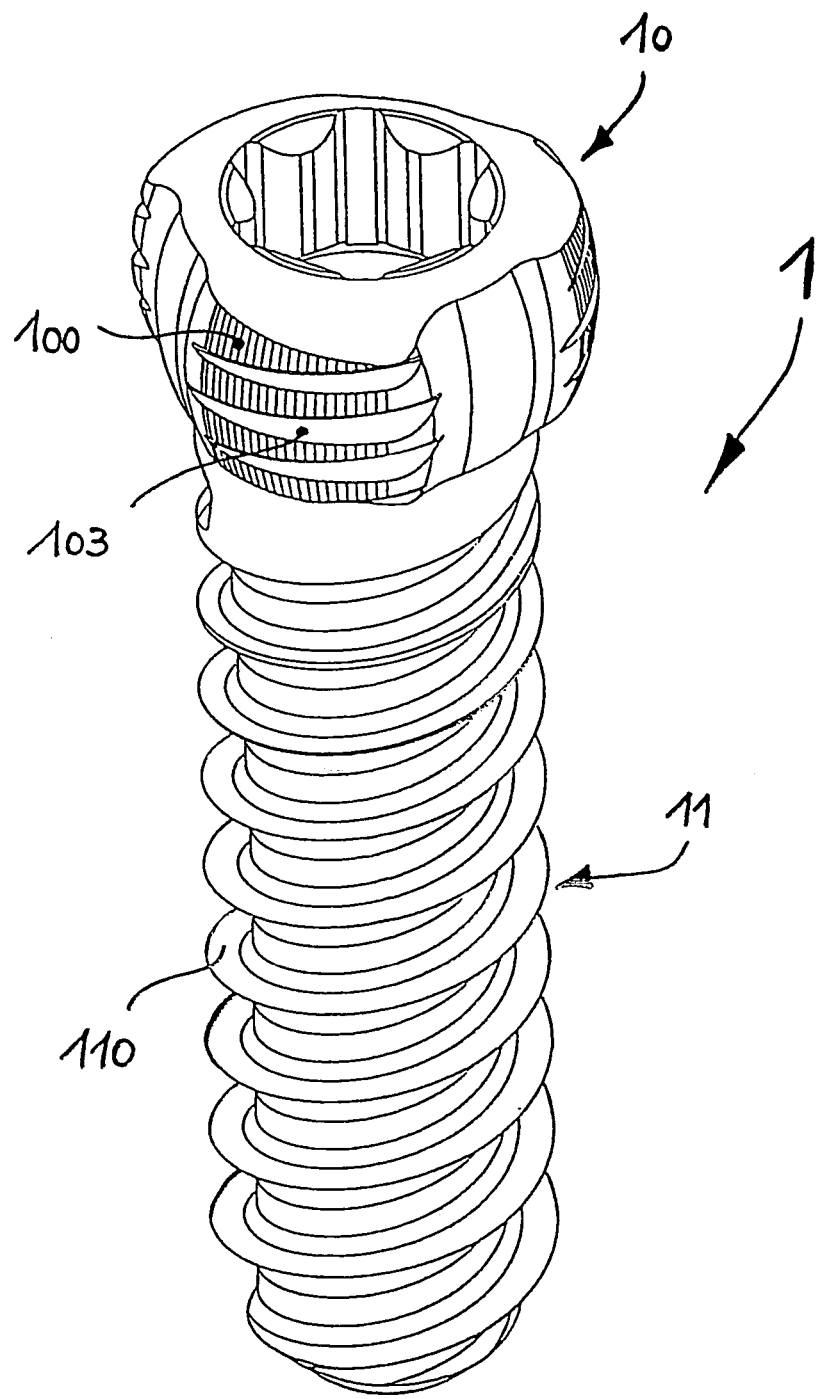
FIG. 24 shows the bone screw from FIG. 1, but with groove-like depressions in the clamping surface of the screw head.

FIG. 24 shows a perspective view of an illustrative embodiment of the screw 1 in which groove-like depressions 103 are provided in the clamping surface 100 of the screw head 10. These groove-like depressions extend substantially in the same direction and substantially with the same pitch as the shank thread 110 on the screw shank. These groove-like depressions 103 can play an important role when the screw 1 is being turned in, as will be explained below.

Let us imagine that the screw shank of the screw from FIG. 24 is to be screwed through the plate aperture 30 into the bone of a patient and that the screw head 10 is to be fixed (locked) in the housing 2 of the bone plate 3 (FIG. 3). Toward the end of the screwing-in operation, that is to say when the screw shank 11 has been screwed substantially into the bone, the screw head 10 engages in the housing 2 of the bone plate 3. As it is not possible to predict in which azimuthal relative position the engagement of the screw head 10 in the housing 2 will take place, situations may arise in which the clamping surface 100 collides with an inwardly projecting region of the housing 2, which projection, due to the contour of the inner wall 200 of the housing 2, is present for example where the regions 203 (core drill of the plate aperture 30) and a run-in/runout contour 201 border one another.

If, in such a scenario, the screw from FIG. 1 were to be screwed in further, the clamping surface 100 could deform this inwardly projecting region to an extent limited by the material (titanium), in which case the material is then no longer able to further deform and the screw head 10 would then be stuck in this position. The wedging effect, however, would not occur where it is actually wanted, namely between the clamping surface 100 and the outwardly widening recess 20 of the inner wall 200, and, as a consequence, this wedging effect would not give the desired surface locking. Moreover, in this region, the contour of the housing and/or the clamping surface 100 of the screw head 10 could be damaged, for which reason the connection between screw 1 and bone plate 3 may be less stable in such cases than when the desired locking is present. In addition, it is possible that the loosening, repositioning and refixing (locking) of the bone fragments, as already described with reference to FIGS. 12-19, is then no longer possible because of damage caused to the screw 1 and/or the housing 2 of the bone plate 3. For the operating physician, it is then difficult, if not impossible, to ascertain whether the wedging effect represents a correct, desired locking of the screw head 10 in the housing 2 or is the above-described unwanted wedging effect.

To ensure correct locking of the screw head 10 in the housing 2 of the bone plate 3 even in those rare cases in which the above-described scenario arises, groove-like depressions 103 are provided in the clamping surface 100. As has already been mentioned above, the groove-like depressions 103 extend substantially in the same direction and substantially with the same pitch as the shank thread 110. This is because, when the screw 1 is screwed in farther, the screw head 10, and thus also the clamping surface 100, is moved according to the pitch of the shank thread both in the azimuthal direction and in the axial direction. The unwanted wedging effect, as described above, is now prevented by the fact that the inwardly projecting region of the housing 2 can slide into one of the groove-like depressions 103. By virtue of the course and pitch of the groove-like depressions 103, the inwardly projecting region is then channeled by the groove-like depression 103 into which it has slid, because the continued screwing-in of the screw 1 has the effect that the axial and azimuthal movement of the screw head 10 always takes place at the same extent to which the shank thread 110 penetrates into the bone. After this channeling action, the screw runs free again, i.e. for a short time there is no contact between housing and screw head. Upon further screwing-in, the above-described locking then takes place. Despite the presence of the groove-like depressions 103, a sufficiently large clamping surface 100 remains to ensure good locking of the screw head 10 in the housing 2 of the bone plate 3.

Figure 25:
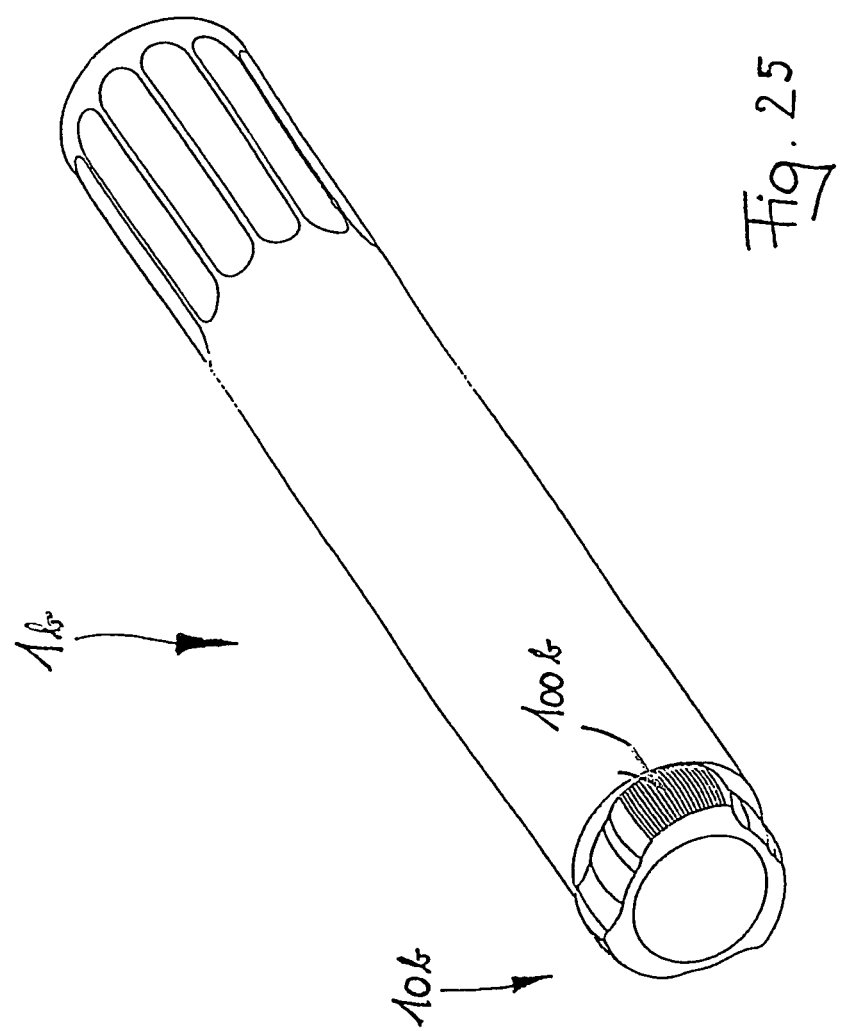
FIG. 25 shows a further illustrative embodiment of a locking element in the form of a drill guide, which can be locked for example in the plate aperture of a bone plate.

FIG. 25 shows a further illustrative embodiment of a locking element in the form of a drill guide 1b. The drill guide 1b is provided with a locking part 10b which is designed similarly to the screw head 10 of the bone screw 1 and therefore, in particular, can also be locked at different angles relative to the longitudinal axis of the housing or plate aperture. For this purpose, the locking part 10b is provided with clamping surfaces 100b which can be locked in the housing 2 in the same way as described above for the clamping surfaces 100 of the screw head 10. Through the locked drill guide it is then possible, for example, to guide a drill with which a bore for a bone screw is formed in the bone at a suitable angle (that can be chosen freely through the arrangement of the drill template).

Figure 26:
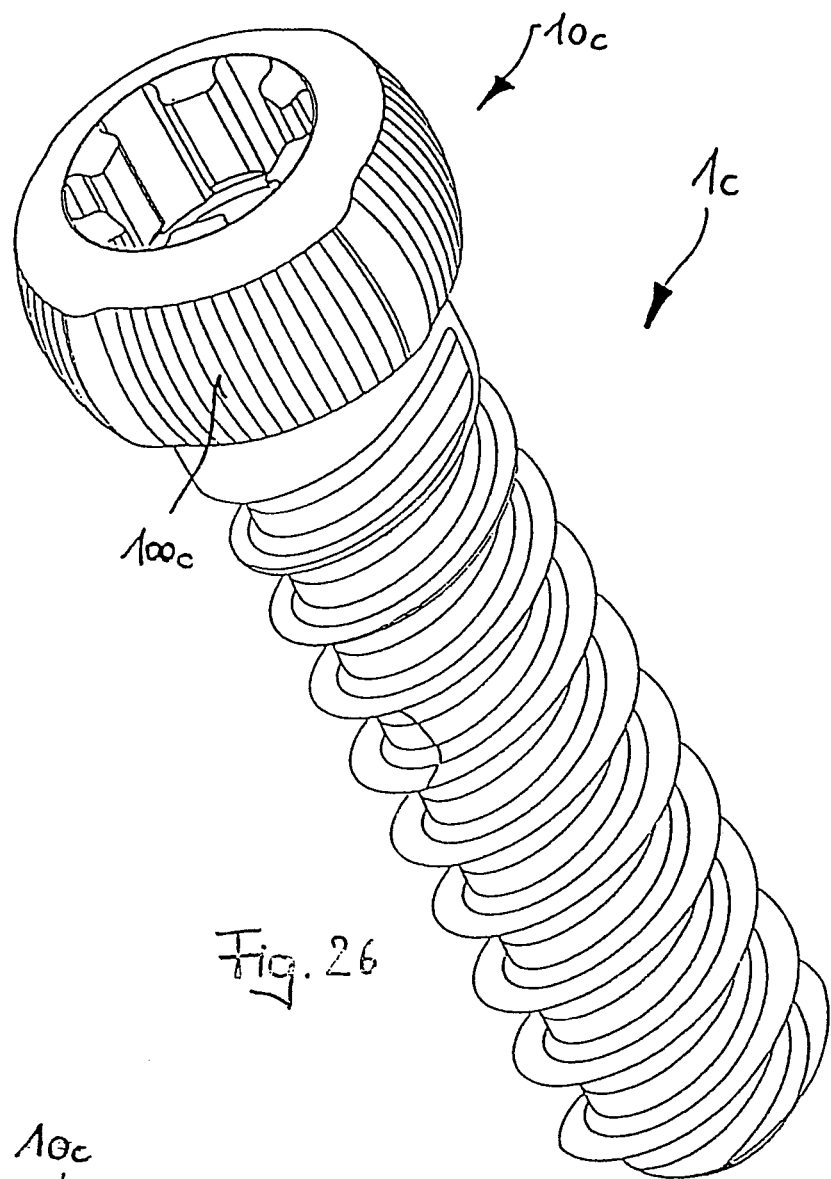
FIG. 26 shows a further illustrative embodiment of a locking element in the form of a bone screw, with four clamping areas arranged uniformly on the circumference of the screw head.
Figure 27:
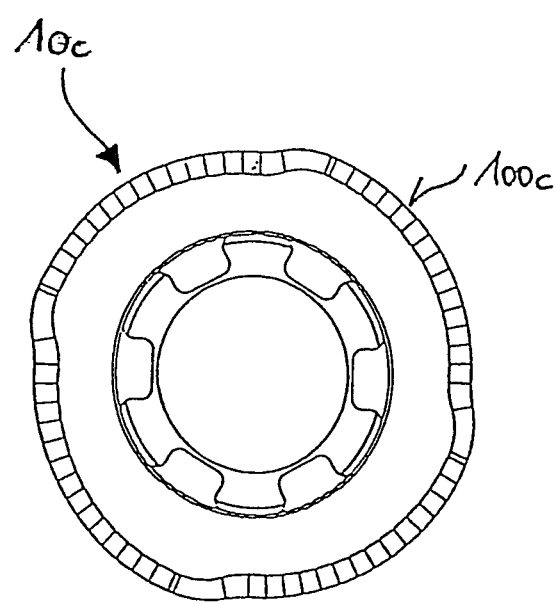
FIG. 27 shows a plan view of the bone screw from FIG. 26.

FIG. 26 shows a further illustrative embodiment of a locking element in the form of a further bone screw 1c, which differs from the bone screw 1 essentially in that the screw head 10c does not have three clamping areas, but instead four clamping areas 100c distributed uniformly about the circumference. This can also be clearly seen from the plan view in FIG. 27. The associated housing (not shown) then preferably also has four recesses for locking the screw 1c in the associated housing.

Figure 28:
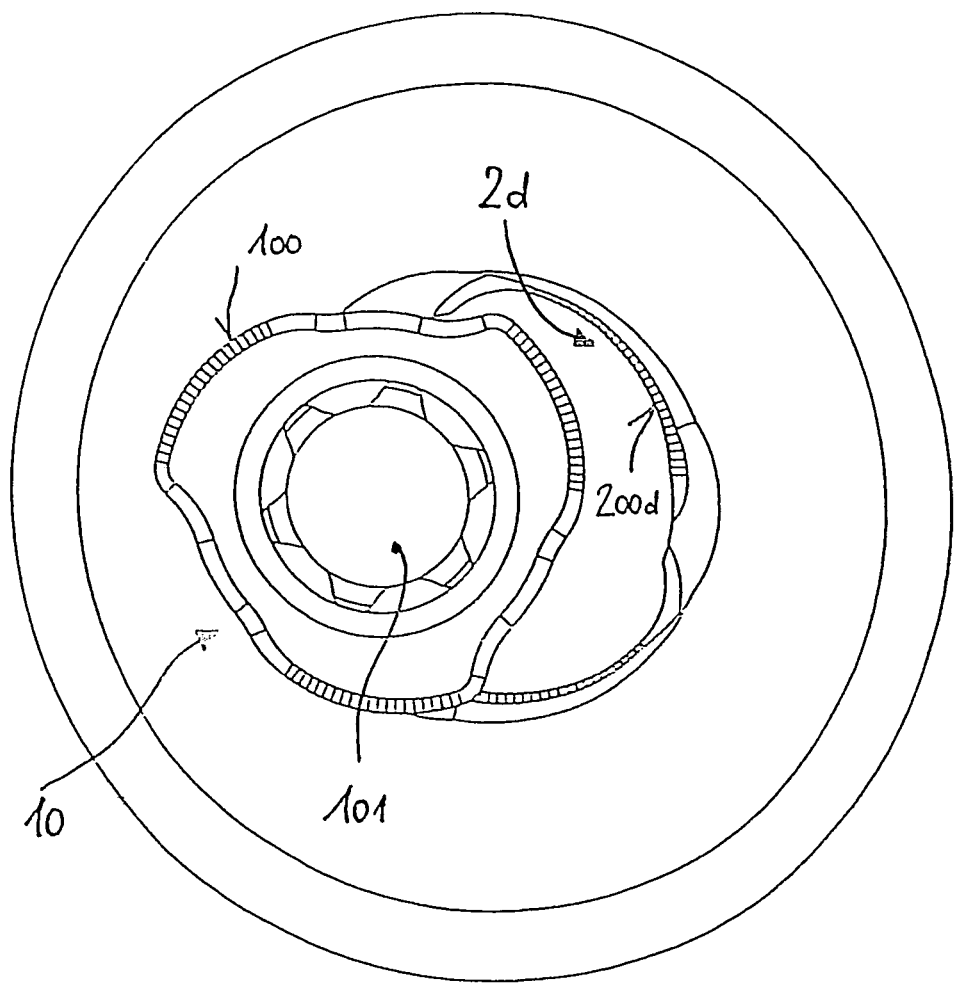
FIG. 28 shows a plan view of a further illustrative embodiment of a housing in an oblong hole of a bone plate, which for example can be used in compression osteosynthesis, with an associated bone screw, in the unlocked position before the start of compression.
Figure 29:
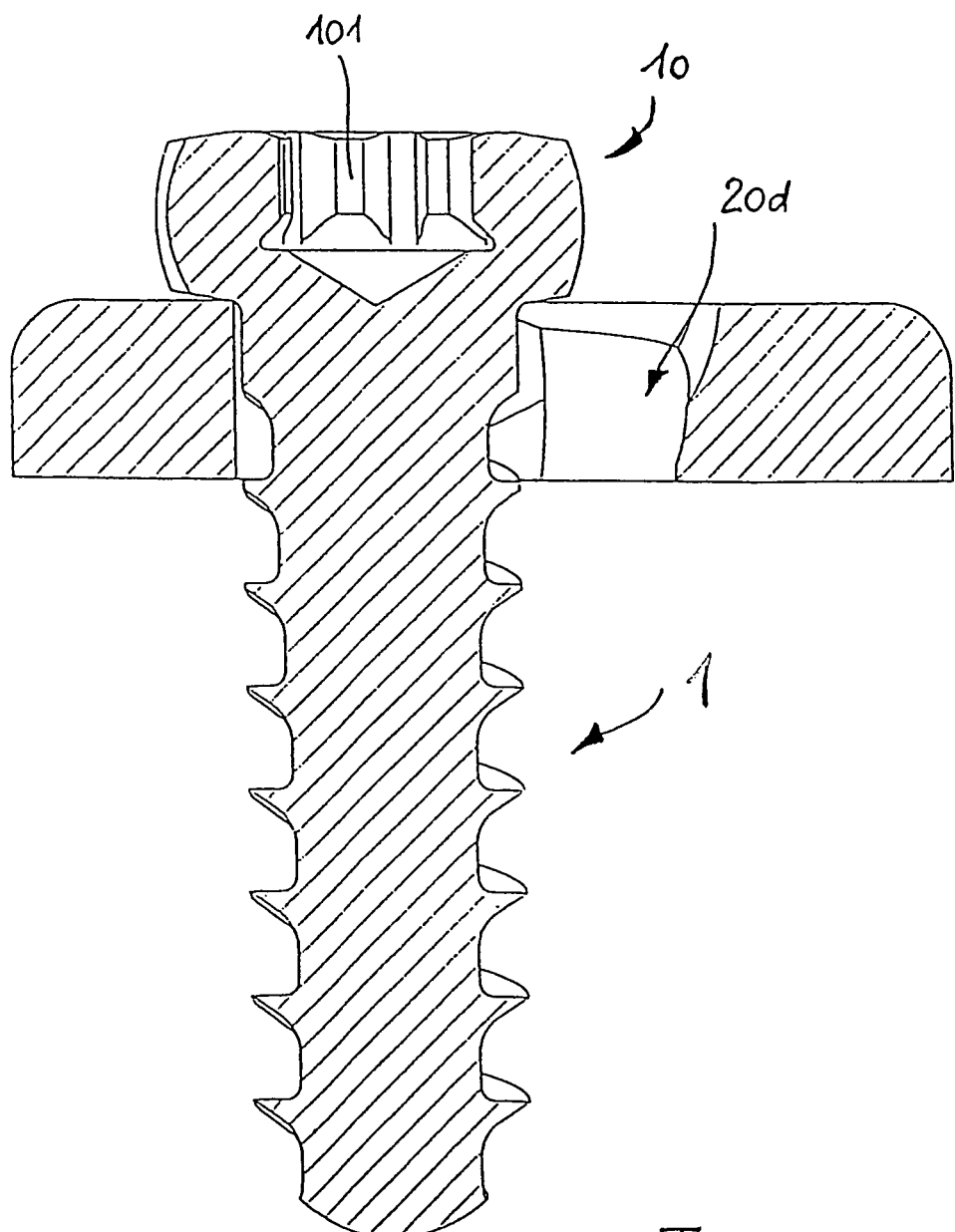
FIG. 29 shows the illustrative embodiment from FIG. 28 in longitudinal section.

FIG. 28 shows a plan view of a further illustrative embodiment of a housing 2d in an oblong hole 30d of a bone plate which, for example, can be used in compression osteosynthesis. FIG. 29 shows a corresponding view in longitudinal section. The associated bone screw 1 is also shown in the unlocked position at the start of compression. The housing 2d is likewise provided with recesses 20d whose inner walls 200d can in principle be designed in the same way as the inner wall 200 of the recesses 20 already explained above. Likewise, the screw 1 is provided with clamping surfaces 100 on the screw head 10.

Figure 30:
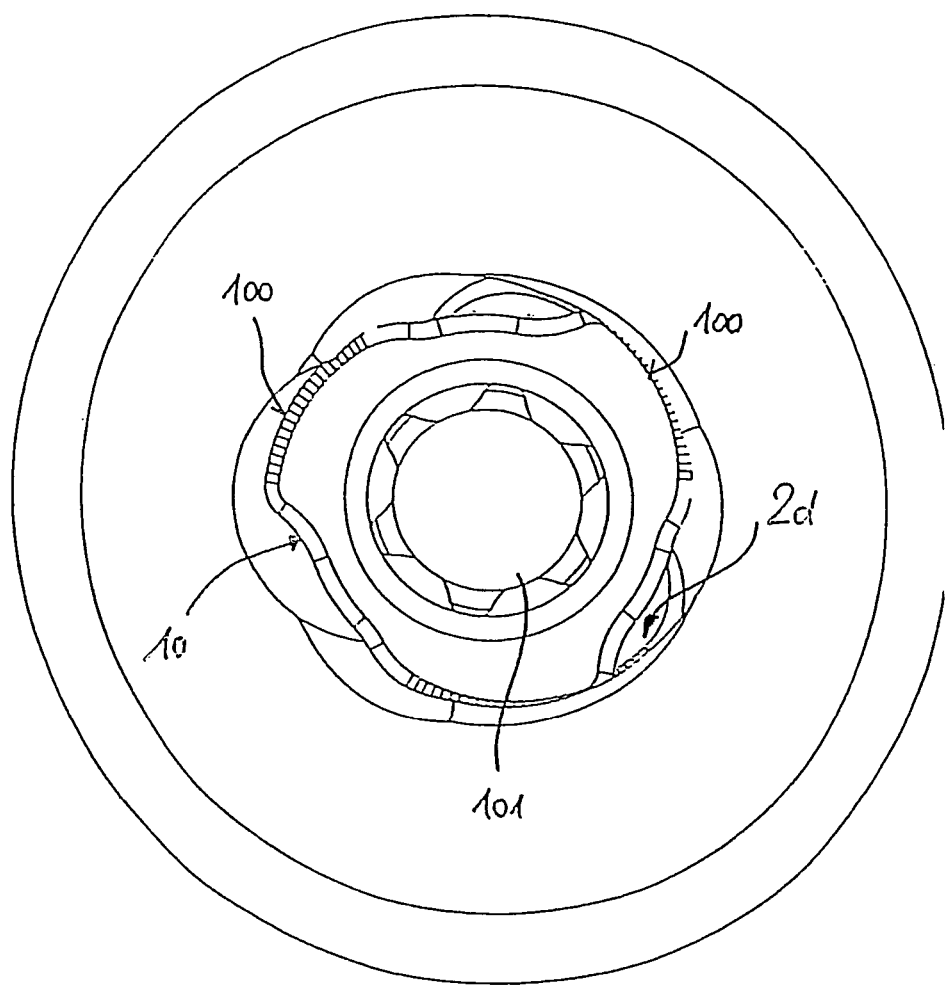
FIG. 30 shows the plan view corresponding to FIG. 28, the screw and bone plate being locked in the compression position.
Figure 31:
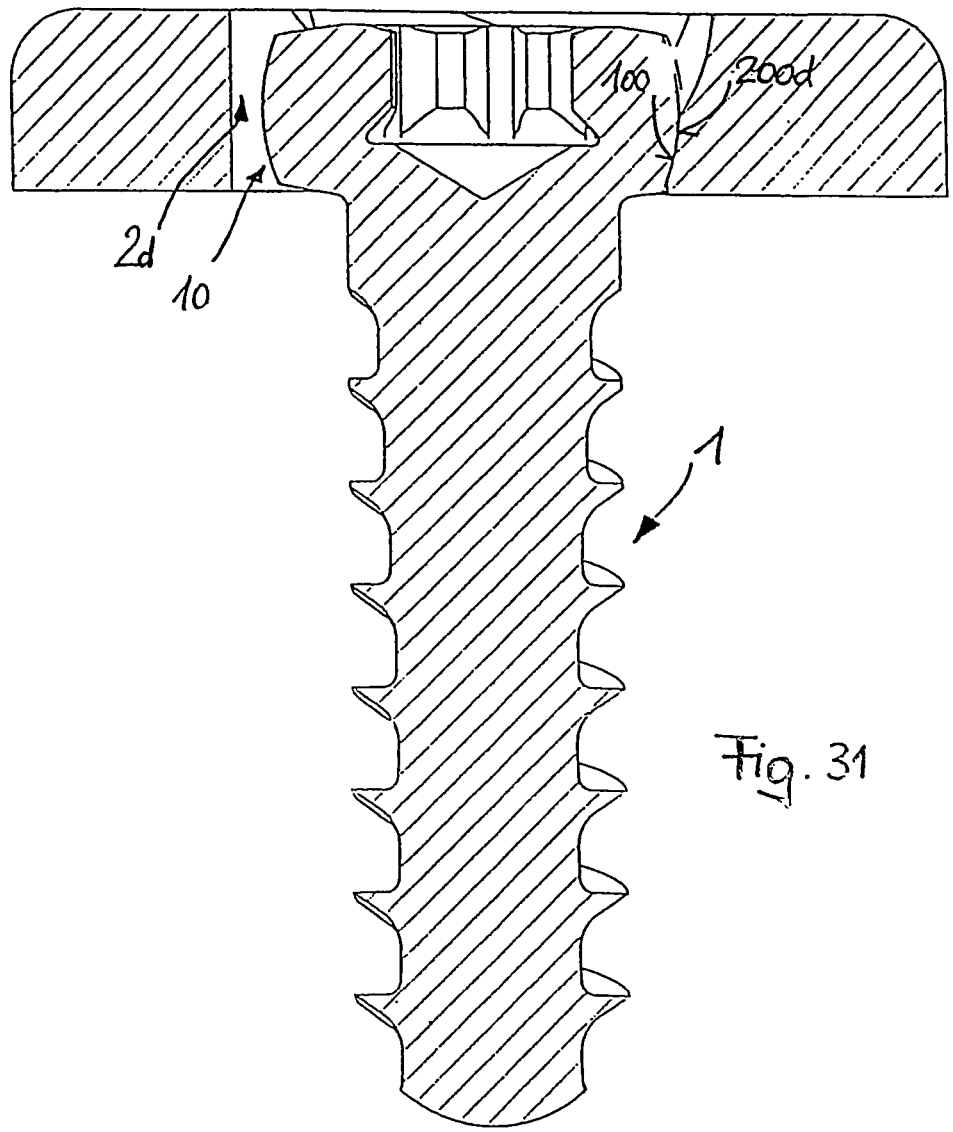
FIG. 31 shows the longitudinal section corresponding to FIG. 29, the screw and bone plate being locked.

In compression osteosynthesis, the following procedure, for example, can be followed. The bone screw 1 is already screwed into one of two bone segments on either side of a fracture, and the other bone segment is already connected fixedly to the bone plate by means of a bone screw. By turning the bone screw (engagement of a tool in the socket contour 101), the screw 1 now slides into the housing 2d. The bone segment connected to the screw 1d is thus pressed against the bone segment already fixedly connected to the plate by means of a screw. In this position, the screw 1 is locked in the housing 2d in the manner already described above. This situation is also shown in the plan view according to FIG. 30 and in the longitudinal section according to FIG. 31.

Figure 32:
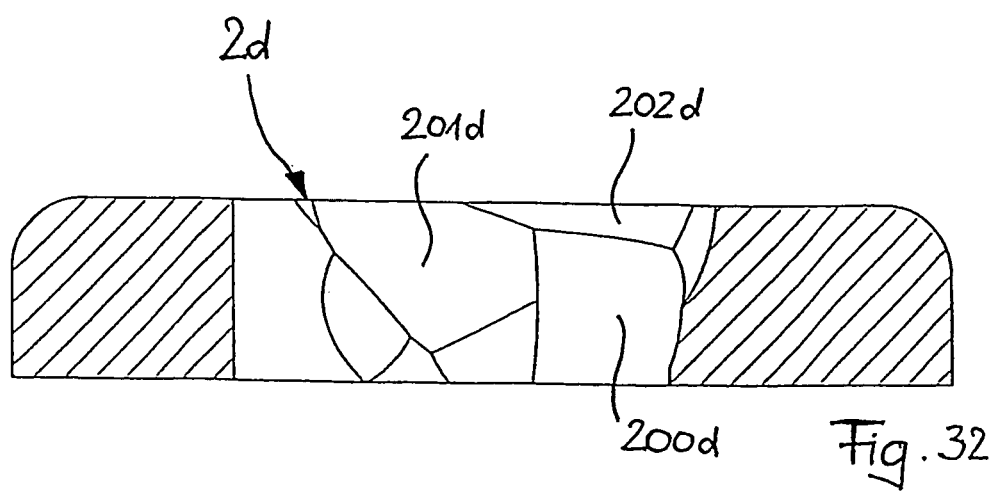
FIG. 32 shows a longitudinal section through the housing from FIG. 31.

FIG. 32 finally shows another longitudinal section through the housing 2d of the oblong hole. Besides the inner wall 200d for locking with the clamping surface 100 of the bone screw 1 (not shown here), this figure also shows the runout surface 201d, whose function has also already been described above (guiding a screw out after the locking has been released), and the countersink 202d for receiving a conventional bone screw with which, of course, compression osteosynthesis is likewise possible in a conventional manner (albeit without locking).

Figure 33:
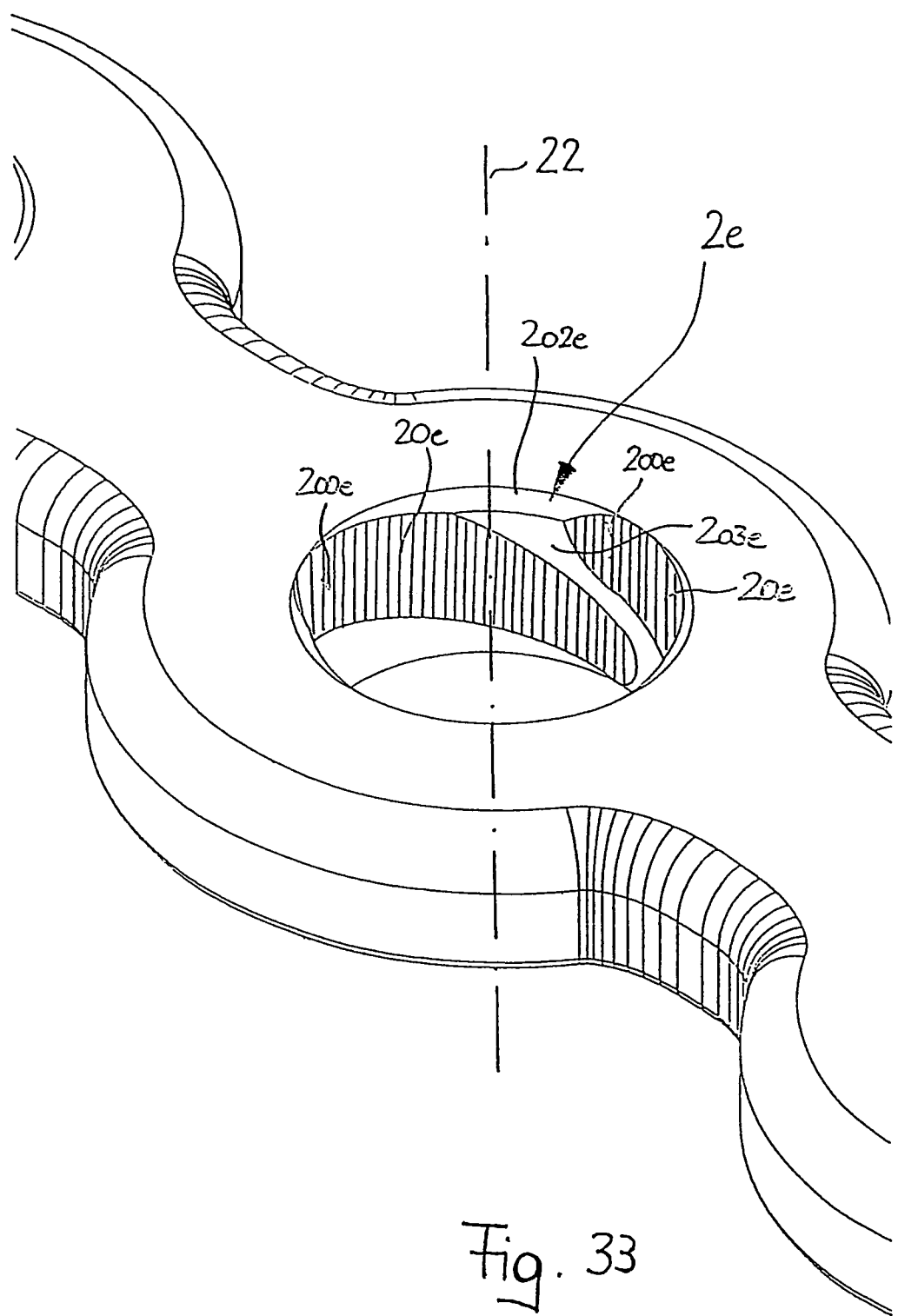
FIG. 33 shows a perspective view of a detail from a bone plate, with a further illustrative embodiment of a housing according to the invention in the plate aperture (recess extending in the manner of a spatial spiral).

FIG. 33 shows, in a perspective view, a detail from a bone plate with a further illustrative embodiment of a housing 2e according to the invention in the plate aperture. In this illustrative embodiment of the housing 2e, the recess 20e does not extend in a direction perpendicular to the longitudinal axis 22 of the housing (i.e. not horizontally), as in the illustrative embodiment according to FIG. 3 and FIG. 4, but instead extends in the manner of a spatial spiral about the longitudinal axis. Besides the inner wall 200e in the region of the recess 20e, FIG. 33 also shows the spherical countersink 202e for receiving a screw head of a conventional bone screw with a spherical underside of the head, and the region 203e of the cylindrical core drill. In the illustrative embodiment shown, no runout contour is provided, although in principle it could be, for example if the spatial spiral has only a very slight pitch which does not permit simple removal of the screw.

By contrast, the associated screw remains as already described above. As the screw is turned in, the screw head is therefore not guided along the recess in the horizontal direction, as is the case in the illustrative embodiment according to FIG. 3 and FIG. 4, but instead along the spatial spiral of the recess. The tiltable nature of the screw is also provided for here, and the locking takes place in the same way as already described. The above description concerns, by way of example, the locking of bone screws in housings of corresponding bone plates.

It should further be noted that the present invention is not limited to this field of application, and instead generally concerns the locking of a locking element in a corresponding housing, which may also be entirely desirable in other fields of application, as was discussed in the introduction.

Specific embodiments of a housing for a locking element and locking element according to the present invention have been described for the purpose of illustrating the manner in which the invention may be made and used. It should be understood that implementation of other variations and modifications of the invention and its various aspects will be apparent to those skilled in the art, and that the invention is not limited by the specific embodiments described. It is therefore contemplated to cover by the present invention any and all modifications, variations, or equivalents that fall within the true spirit and scope of the basic underlying principles disclosed and claimed herein.

The invention claimed is:

1. A surgical housing for a locking element, with a peripheral inner wall which extends substantially in the direction of a longitudinal axis of the housing, wherein at least one recess is formed in the peripheral inner wall, the recess widening outward thereby defining a wedge shape, wherein a radius between the longitudinal axis and the peripheral inner wall, where the peripheral inner wall forms one of the at least one recesses, increases in an azimuth plane as a function of a revolution angle around said longitudinal axis, wherein said increase is described by part of: a logarithmic spiral, a circular trajectory, an involute, or a function of the type $r = a_1 + b_1 \sqrt{\alpha}$, where r is the respective distance of the peripheral inner wall from the longitudinal axis of the housing, $a_1$ and $b_1$ are constants, and $\alpha$ stands for the respective angle of revolution, and wherein the peripheral inner wall is at least substantially spherical, paraboloidal, or ellipsoidal, in the region of the recess and, upon locking, permits a radial wedging between the recess and an outer contour of a locking part of the locking element.

2. The housing as claimed in claim 1, wherein the recess is arranged such that it extends in a direction perpendicular to the longitudinal axis of the housing.

3. The housing as claimed in claim 1, wherein the peripheral inner wall has three recesses which are distributed uniformly along its circumference and which each widen outward in a wedge shape from the longitudinal axis of the housing.

4. The housing as claimed in claim 1, wherein the housing has, on its peripheral inner wall, a runout contour which adjoins the recess or recesses in a circumferential direction and is used for guiding the locking element out of the housing.

5. The housing as claimed in claim 1, wherein the housing is provided with a countersink for receiving a screw head with a spherical underside.

6. The housing as claimed in claim 1, wherein the at least one recess widening outward defining a wedge shape is configured as spatial spiral around the longitudinal axis on the peripheral inner wall of the housing.

7. A bone plate with plate apertures, at least one plate aperture constituting a housing, for a locking element which is to be locked with the bone plate, wherein the housing is designed according to claim 1.

8. A locking element for introduction into a housing and for locking with said housing, which locking element comprises a locking part, which is provided with a peripheral outer surface which extends substantially in a direction of a longitudinal axis of the locking element and has at least one clamping surface in a region of which, viewed in an azimuth plane perpendicular to the longitudinal axis, a distance of the outer surface increases outward from the longitudinal axis as a function of an angle of revolution about the longitudinal axis in a wedge shape, in order to be able to lock the locking part of the locking element with a corresponding inner contour of the housing, wherein the peripheral outer surface is at least substantially spherical, paraboloidal, or ellipsoidal, at least in the region of the clamping surface and, upon locking, permits radial wedging between the clamping surface and the corresponding inner contour of the housing.

9. The locking element as claimed in claim 8, wherein the peripheral outer surface has three clamping surfaces which are distributed uniformly along its circumference.

10. The locking element as claimed in claim 8, wherein a contour of the peripheral outer surface in the region of the clamping surface or clamping surfaces is described in an azimuth plane by part of a logarithmic spiral, by part of a circular trajectory, or by part of an involute.

11. The locking element as claimed in claim 8, wherein at least the clamping surface of the locking element is additionally provided with peripheral grooves.

12. The locking element as claimed in claim 8, wherein the locking element is a surgical locking element.

13. The locking element as claimed in claim 8, wherein the locking part does not contain a thread.

14. The locking element as claimed in claim 8, wherein a contour of the outer surface, in the region of the clamping surface or clamping surfaces widening outward in a wedge shape from the longitudinal axis, can be described in an azimuth plane by a function of the type $r = a_2 + b_2 \sqrt{\alpha}$, where r is the respective distance of the clamping surface from the longitudinal axis, $a_2$ and $b_2$ are constants, and $\alpha$ stands for the respective azimuth angle, or wherein the contour of the outer surface, in the region of the clamping surface or clamping surfaces widening outward in a wedge shape from the longitudinal axis, can be described in an azimuth plane by part of a logarithmic spiral, by part of a circular trajectory, or by part of an involute.

15. A screw with a screw shank which is provided at least partially with a thread, and with a screw head which protrudes outward above the shank and the thread, wherein the screw head is provided with a peripheral outer surface which extends substantially in a direction of a longitudinal axis of the screw and has at least one clamping surface in a region of which, viewed in an azimuth plane perpendicular to the longitudinal axis, a distance of the outer surface increases outward from the longitudinal axis as a function of an angle of revolution about the longitudinal axis in a wedge shape, in order to be able to lock the screw head with a corresponding inner contour of a housing, wherein the peripheral outer surface is at least substantially spherical, paraboloidal, or ellipsoidal, at least in the region of the clamping surface and, upon locking, permits radial wedging between the clamping surface and the corresponding inner contour of the housing.

16. The screw as claimed in claim 15, wherein at least one groove-like depression is provided in the at least one clamping surface, which at least one depression extends substantially in a same direction and has substantially a same pitch as the thread protruding outward from the screw shank.

17. The screw as claimed in claim 15, wherein the screw is a bone screw.

18. The screw as claimed in claim 15, wherein the screw head does not contain a thread.

19. The screw as claimed in claim 15, wherein a contour of the outer surface, in the region of the clamping surface or clamping surfaces widening outward in a wedge shape from the longitudinal axis, can be described in an azimuth plane by a function of the type $r = a2 + b2\sqrt{\alpha}$, where r is the respective distance of the clamping surface from the longitudinal axis, a2 and b2 are constants, and $\alpha$ stands for the respective azimuth angle, or wherein the contour of the outer surface, in the region of the clamping surface or clamping surfaces widening outward in a wedge shape from the longitudinal axis, can be described in an azimuth plane by part of a logarithmic spiral, by part of a circular trajectory, or by part of an involute.

20. A set of bone plates and screws containing at least one bone plate according to claim 7.

21. A bone plate with plate apertures, wherein at least one plate aperture is designed as an oblong hole, and is provided with a housing for a locking element which is to be locked with the bone plate, wherein the housing is designed according to claim 1.

* * * * *